US 6,472,155 B1
(12) United States Patent
McKinney

(10) Patent No.: US 6,472,155 B1
(45) Date of Patent: Oct. 29, 2002

(54) SPECIES SPECIFIC IDENTIFICATION OF SPORE-PRODUCING MICROBES USING THE GENE SEQUENCE OF SMALL ACID-SOLUBLE SPORE COAT PROTEINS FOR AMPLIFICATION BASED DIAGNOSTICS

(75) Inventor: Nancy McKinney, Decatur, GA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 09/590,759

(22) Filed: Jun. 8, 2000

Related U.S. Application Data
(60) Provisional application No. 60/138,167, filed on Jun. 8, 1999, and provisional application No. 60/192,206, filed on Mar. 27, 2000.

(51) Int. Cl.[7] ................................................ C12Q 1/68
(52) U.S. Cl. ........................ 435/6; 435/91.1; 435/91.2; 536/23.1; 536/22.1
(58) Field of Search ........................ 435/6, 91.1, 91.2; 536/23.1, 22.1

(56) References Cited

U.S. PATENT DOCUMENTS 5,985,557 A * 11/1999 Prudent et al. ................ 435/6

FOREIGN PATENT DOCUMENTS

WO    WO 95/21912    * 8/1995    .................... 435/6

OTHER PUBLICATIONS

Cabrera–Martinez et al. FEMS Microbiology Letters. vol. 77. pp. 127–132. 1991.*

Sun and Setlow. J. Bacteriology. vol. 169. pp. 308–3093. 1987.*

* cited by examiner

Primary Examiner—W. Gary Jones
Assistant Examiner—Janell E. Taylor
(74) Attorney, Agent, or Firm—John W. Mahoney; David J. Aston; Michelle S. Chew

(57) ABSTRACT

PCR (polymerase chain reaction) primers for the detection of certain Bacillus species, such as *Bacillus anthracis*. The primers specifically amplify only DNA found in the target species and can distinguish closely related species. Species-specific PCR primers for *Bacillus anthracis, Bacillus globigii* and *Clostridium perfringens* are disclosed. The primers are directed to unique sequences within sasp (small acid soluble protein) genes.

15 Claims, 7 Drawing Sheets

Figure 1A

ClustalW DNA Sequence Alignment of *sasp-B* Amplicons from 38 *Bacillus anthracis* Strains

```
             1              15 16             30 31             45 46             60 61             75 76             90
 1 Bapast    AACAAGGCAACTTCT GGTGCTAGCATTCAA AGCACACAAATGCTAGT TATGGTACAGAGTTT GCGACTGAAACAAAT GTACAAGCAGTAAAA
 2 Barec1    AACAAGGCAACTTCT GGTGCTAGCATTCAA AGCACACAAATGCTAGT TATGGTACAGAGTTT GCGACTGAAACAAAT GTACAAGCAGTAAAA
 3 NMRI#67   AACAAGGCAACTTCT GGTGCTAGCATTCAA AGCACACAAATGCTAGT TATGGTACAGAGTTT GCGACTGAAACAAAT GTACAAGCAGTAAAA
 4 NMRI#63   AACAAGGCAACTTCT GGTGCTAGCATTCAA AGCACACAAATGCTAGT TATGGTACAGAGTTT GCGACTGAAACAAAT GTACAAGCAGTAAAA
 5 NMRI#62   AACAAGGCAACTTCT GGTGCTAGCATTCAA AGCACACAAATGCTAGT TATGGTACAGAGTTT GCGACTGAAACAAAT GTACAAGCAGTAAAA
 6 NMRI#60   AACAAGGCAACTTCT GGTGCTAGCATTCAA AGCACACAAATGCTAGT TATGGTACAGAGTTT GCGACTGAAACAAAT GTACAAGCAGTAAAA
 7 NMRI#1    AACAAGGCAACTTCT GGTGCTAGCATTCAA AGCACACAAATGCTAGT TATGGTACAGAGTTT GCGACTGAAACAAAT GTACAAGCAGTAAAA
 8 NMRI#2    AACAAGGCAACTTCT GGTGCTAGCATTCAA AGCACACAAATGCTAGT TATGGTACAGAGTTT GCGACTGAAACAAAT GTACAAGCAGTAAAA
 9 NMRI#4    AACAAGGCAACTTCT GGTGCTAGCATTCAA AGCACACAAATGCTAGT TATGGTACAGAGTTT GCGACTGAAACAAAT GTACAAGCAGTAAAA
10 NMRI#5    AACAAGGCAACTTCT GGTGCTAGCATTCAA AGCACACAAATGCTAGT TATGGTACAGAGTTT GCGACTGAAACAAAT GTACAAGCAGTAAAA
11 NMRI#6    AACAAGGCAACTTCT GGTGCTAGCATTCAA AGCACACAAATGCTAGT TATGGTACAGAGTTT GCGACTGAAACAAAT GTACAAGCAGTAAAA
12 NMRI#10   AACAAGGCAACTTCT GGTGCTAGCATTCAA AGCACACAAATGCTAGT TATGGTACAGAGTTT GCGACTGAAACAAAT GTACAAGCAGTAAAA
13 NMRI#11   AACAAGGCAACTTCT GGTGCTAGCATTCAA AGCACACAAATGCTAGT TATGGTACAGAGTTT GCGACTGAAACAAAT GTACAAGCAGTAAAA
14 NMRI#18   AACAAGGCAACTTCT GGTGCTAGCATTCAA AGCACACAAATGCTAGT TATGGTACAGAGTTT GCGACTGAAACAAAT GTACAAGCAGTAAAA
15 NMRI#19   AACAAGGCAACTTCT GGTGCTAGCATTCAA AGCACACAAATGCTAGT TATGGTACAGAGTTT GCGACTGAAACAAAT GTACAAGCAGTAAAA
16 NMRI#20   AACAAGGCAACTTCT GGTGCTAGCATTCAA AGCACACAAATGCTAGT TATGGTACAGAGTTT GCGACTGAAACAAAT GTACAAGCAGTAAAA
17 NMRI#22   AACAAGGCAACTTCT GGTGCTAGCATTCAA AGCACACAAATGCTAGT TATGGTACAGAGTTT GCGACTGAAACAAAT GTACAAGCAGTAAAA
18 NMRI#23   AACAAGGCAACTTCT GGTGCTAGCATTCAA AGCACACAAATGCTAGT TATGGTACAGAGTTT GCGACTGAAACAAAT GTACAAGCAGTAAAA
19 NMRI#24   AACAAGGCAACTTCT GGTGCTAGCATTCAA AGCACACAAATGCTAGT TATGGTACAGAGTTT GCGACTGAAACAAAT GTACAAGCAGTAAAA
20 NMRI#25   AACAAGGCAACTTCT GGTGCTAGCATTCAA AGCACACAAATGCTAGT TATGGTACAGAGTTT GCGACTGAAACAAAT GTACAAGCAGTAAAA
21 NMRI#26   AACAAGGCAACTTCT GGTGCTAGCATTCAA AGCACACAAATGCTAGT TATGGTACAGAGTTT GCGACTGAAACAAAT GTACAAGCAGTAAAA
22 NMRI#28   AACAAGGCAACTTCT GGTGCTAGCATTCAA AGCACACAAATGCTAGT TATGGTACAGAGTTT GCGACTGAAACAAAT GTACAAGCAGTAAAA
23 NMRI#32   AACAAGGCAACTTCT GGTGCTAGCATTCAA AGCACACAAATGCTAGT TATGGTACAGAGTTT GCGACTGAAACAAAT GTACAAGCAGTAAAA
24 NMRI#35   AACAAGGCAACTTCT GGTGCTAGCATTCAA AGCACACAAATGCTAGT TATGGTACAGAGTTT GCGACTGAAACAAAT GTACAAGCAGTAAAA
25 NMRI#36   AACAAGGCAACTTCT GGTGCTAGCATTCAA AGCACACAAATGCTAGT TATGGTACAGAGTTT GCGACTGAAACAAAT GTACAAGCAGTAAAA
26 NMRI#38   AACAAGGCAACTTCT GGTGCTAGCATTCAA AGCACACAAATGCTAGT TATGGTACAGAGTTT GCGACTGAAACAAAT GTACAAGCAGTAAAA
27 NMRI#39   AACAAGGCAACTTCT GGTGCTAGCATTCAA AGCACACAAATGCTAGT TATGGTACAGAGTTT GCGACTGAAACAAAT GTACAAGCAGTAAAA
28 NMRI#40   AACAAGGCAACTTCT GGTGCTAGCATTCAA AGCACACAAATGCTAGT TATGGTACAGAGTTT GCGACTGAAACAAAT GTACAAGCAGTAAAA
29 NMRI#41   AACAAGGCAACTTCT GGTGCTAGCATTCAA AGCACACAAATGCTAGT TATGGTACAGAGTTT GCGACTGAAACAAAT GTACAAGCAGTAAAA
30 NMRI#42   AACAAGGCAACTTCT GGTGCTAGCATTCAA AGCACACAAATGCTAGT TATGGTACAGAGTTT GCGACTGAAACAAAT GTACAAGCAGTAAAA
31 NMRI#43   AACAAGGCAACTTCT GGTGCTAGCATTCAA AGCACACAAATGCTAGT TATGGTACAGAGTTT GCGACTGAAACAAAT GTACAAGCAGTAAAA
32 NMRI#50   AACAAGGCAACTTCT GGTGCTAGCATTCAA AGCACACAAATGCTAGT TATGGTACAGAGTTT GCGACTGAAACAAAT GTACAAGCAGTAAAA
33 NMRI#52   AACAAGGCAACTTCT GGTGCTAGCATTCAA AGCACACAAATGCTAGT TATGGTACAGAGTTT GCGACTGAAACAAAT GTACAAGCAGTAAAA
34 NMRI#53   AACAAGGCAACTTCT GGTGCTAGCATTCAA AGCACACAAATGCTAGT TATGGTACAGAGTTT GCGACTGAAACAAAT GTACAAGCAGTAAAA
35 NMRI#54   AACAAGGCAACTTCT GGTGCTAGCATTCAA AGCACACAAATGCTAGT TATGGTACAGAGTTT GCGACTGAAACAAAT GTACAAGCAGTAAAA
36 NMRI#55   AACAAGGCAACTTCT GGTGCTAGCATTCAA AGCACACAAATGCTAGT TATGGTACAGAGTTT GCGACTGAAACAAAT GTACAAGCAGTAAAA
37 NMRI#56   AACAAGGCAACTTCT GGTGCTAGCATTCAA AGCACACAAATGCTAGT TATGGTACAGAGTTT GCGACTGAAACAAAT GTACAAGCAGTAAAA
38 NMRI#59   AACAAGGCAACTTCT GGTGCTAGCATTCAA AGCACACAAATGCTAGT TATGGTACAGAGTTT GCGACTGAAACAAAT GTACAAGCAGTAAAA
```

Figure 1B

ClustalW DNA Sequence Alignment of *sasp-B* Amplicons from 38 *Bacillus anthracis* Strains

```
            91            105 106           120 121           135 136           150 151           165 166           180
 1 Bapast   CAAGCAAACGCACAA TCAGAAGCTAAGAAA GCGCAAGCTTCTGGT GCTAGCATTCAAAGC ACAAATGCTAGTTAT GGTACAGAATTTGCA
 2 Barec1   CAAGCAAACGCACAA TCAGAAGCTAAGAAA GCGCAAGCTTCTGGT GCTAGCATTCAAAGC ACAAATGCTAGTTAT GGTACAGAATTTGCA
 3 NMRI#67  CAAGCAAACGCACAA TCAGAAGCTAAGAAA GCGCAAGCTTCTGGT GCTAGCATTCAAAGC ACAAATGCTAGTTAT GGTACAGAATTTGCA
 4 NMRI#63  CAAGCAAACGCACAA TCAGAAGCTAAGAAA GCGCAAGCTTCTGGT GCTAGCATTCAAAGC ACAAATGCTAGTTAT GGTACAGAATTTGCA
 5 NMRI#62  CAAGCAAACGCACAA TCAGAAGCTAAGAAA GCGCAAGCTTCTGGT GCTAGCATTCAAAGC ACAAATGCTAGTTAT GGTACAGAATTTGCA
 6 NMRI#60  CAAGCAAACGCACAA TCAGAAGCTAAGAAA GCGCAAGCTTCTGGT GCTAGCATTCAAAGC ACAAATGCTAGTTAT GGTACAGAATTTGCA
 7 NMRI#1   CAAGCAAACGCACAA TCAGAAGCTAAGAAA GCGCAAGCTTCTGGT GCTAGCATTCAAAGC ACAAATGCTAGTTAT GGTACAGAATTTGCA
 8 NMRI#2   CAAGCAAACGCACAA TCAGAAGCTAAGAAA GCGCAAGCTTCTGGT GCTAGCATTCAAAGC ACAAATGCTAGTTAT GGTACAGAATTTGCA
 9 NMRI#4   CAAGCAAACGCACAA TCAGAAGCTAAGAAA GCGCAAGCTTCTGGT GCTAGCATTCAAAGC ACAAATGCTAGTTAT GGTACAGAATTTGCA
10 NMRI#5   CAAGCAAACGCACAA TCAGAAGCTAAGAAA GCGCAAGCTTCTGGT GCTAGCATTCAAAGC ACAAATGCTAGTTAT GGTACAGAATTTGCA
11 NMRI#6   CAAGCAAACGCACAA TCAGAAGCTAAGAAA GCGCAAGCTTCTGGT GCTAGCATTCAAAGC ACAAATGCTAGTTAT GGTACAGAATTTGCA
12 NMRI#10  CAAGCAAACGCACAA TCAGAAGCTAAGAAA GCGCAAGCTTCTGGT GCTAGCATTCAAAGC ACAAATGCTAGTTAT GGTACAGAATTTGCA
13 NMRI#11  CAAGCAAACGCACAA TCAGAAGCTAAGAAA GCGCAAGCTTCTGGT GCTAGCATTCAAAGC ACAAATGCTAGTTAT GGTACAGAATTTGCA
14 NMRI#18  CAAGCAAACGCACAA TCAGAAGCTAAGAAA GCGCAAGCTTCTGGT GCTAGCATTCAAAGC ACAAATGCTAGTTAT GGTACAGAATTTGCA
15 NMRI#19  CAAGCAAACGCACAA TCAGAAGCTAAGAAA GCGCAAGCTTCTGGT GCTAGCATTCAAAGC ACAAATGCTAGTTAT GGTACAGAATTTGCA
16 NMRI#20  CAAGCAAACGCACAA TCAGAAGCTAAGAAA GCGCAAGCTTCTGGT GCTAGCATTCAAAGC ACAAATGCTAGTTAT GGTACAGAATTTGCA
17 NMRI#22  CAAGCAAACGCACAA TCAGAAGCTAAGAAA GCGCAAGCTTCTGGT GCTAGCATTCAAAGC ACAAATGCTAGTTAT GGTACAGAATTTGCA
18 NMRI#23  CAAGCAAACGCACAA TCAGAAGCTAAGAAA GCGCAAGCTTCTGGT GCTAGCATTCAAAGC ACAAATGCTAGTTAT GGTACAGAATTTGCA
19 NMRI#24  CAAGCAAACGCACAA TCAGAAGCTAAGAAA GCGCAAGCTTCTGGT GCTAGCATTCAAAGC ACAAATGCTAGTTAT GGTACAGAATTTGCA
20 NMRI#25  CAAGCAAACGCACAA TCAGAAGCTAAGAAA GCGCAAGCTTCTGGT GCTAGCATTCAAAGC ACAAATGCTAGTTAT GGTACAGAATTTGCA
21 NMRI#26  CAAGCAAACGCACAA TCAGAAGCTAAGAAA GCGCAAGCTTCTGGT GCTAGCATTCAAAGC ACAAATGCTAGTTAT GGTACAGAATTTGCA
22 NMRI#28  CAAGCAAACGCACAA TCAGAAGCTAAGAAA GCGCAAGCTTCTGGT GCTAGCATTCAAAGC ACAAATGCTAGTTAT GGTACAGAATTTGCA
23 NMRI#32  CAAGCAAACGCACAA TCAGAAGCTAAGAAA GCGCAAGCTTCTGGT GCTAGCATTCAAAGC ACAAATGCTAGTTAT GGTACAGAATTTGCA
24 NMRI#35  CAAGCAAACGCACAA TCAGAAGCTAAGAAA GCGCAAGCTTCTGGT GCTAGCATTCAAAGC ACAAATGCTAGTTAT GGTACAGAATTTGCA
25 NMRI#36  CAAGCAAACGCACAA TCAGAAGCTAAGAAA GCGCAAGCTTCTGGT GCTAGCATTCAAAGC ACAAATGCTAGTTAT GGTACAGAATTTGCA
26 NMRI#38  CAAGCAAACGCACAA TCAGAAGCTAAGAAA GCGCAAGCTTCTGGT GCTAGCATTCAAAGC ACAAATGCTAGTTAT GGTACAGAATTTGCA
27 NMRI#39  CAAGCAAACGCACAA TCAGAAGCTAAGAAA GCGCAAGCTTCTGGT GCTAGCATTCAAAGC ACAAATGCTAGTTAT GGTACAGAATTTGCA
28 NMRI#40  CAAGCAAACGCACAA TCAGAAGCTAAGAAA GCGCAAGCTTCTGGT GCTAGCATTCAAAGC ACAAATGCTAGTTAT GGTACAGAATTTGCA
29 NMRI#41  CAAGCAAACGCACAA TCAGAAGCTAAGAAA GCGCAAGCTTCTGGT GCTAGCATTCAAAGC ACAAATGCTAGTTAT GGTACAGAATTTGCA
30 NMRI#42  CAAGCAAACGCACAA TCAGAAGCTAAGAAA GCGCAAGCTTCTGGT GCTAGCATTCAAAGC ACAAATGCTAGTTAT GGTACAGAATTTGCA
31 NMRI#43  CAAGCAAACGCACAA TCAGAAGCTAAGAAA GCGCAAGCTTCTGGT GCTAGCATTCAAAGC ACAAATGCTAGTTAT GGTACAGAATTTGCA
32 NMRI#50  CAAGCAAACGCACAA TCAGAAGCTAAGAAA GCGCAAGCTTCTGGT GCTAGCATTCAAAGC ACAAATGCTAGTTAT GGTACAGAATTTGCA
33 NMRI#52  CAAGCAAACGCACAA TCAGAAGCTAAGAAA GCGCAAGCTTCTGGT GCTAGCATTCAAAGC ACAAATGCTAGTTAT GGTACAGAATTTGCA
34 NMRI#53  CAAGCAAACGCACAA TCAGAAGCTAAGAAA GCGCAAGCTTCTGGT GCTAGCATTCAAAGC ACAAATGCTAGTTAT GGTACAGAATTTGCA
35 NMRI#54  CAAGCAAACGCACAA TCAGAAGCTAAGAAA GCGCAAGCTTCTGGT GCTAGCATTCAAAGC ACAAATGCTAGTTAT GGTACAGAATTTGCA
36 NMRI#55  CAAGCAAACGCACAA TCAGAAGCTAAGAAA GCGCAAGCTTCTGGT GCTAGCATTCAAAGC ACAAATGCTAGTTAT GGTACAGAATTTGCA
37 NMRI#56  CAAGCAAACGCACAA TCAGAAGCTAAGAAA GCGCAAGCTTCTGGT GCTAGCATTCAAAGC ACAAATGCTAGTTAT GGTACAGAATTTGCA
38 NMRI#59  CAAGCAAACGCACAA TCAGAAGCTAAGAAA GCGCAAGCTTCTGGT GCTAGCATTCAAAGC ACAAATGCTAGTTAT GGTACAGAATTTGCA
                                                          insertion region
```

Figure 1C

ClustalW DNA Sequence Alignment of *sasp-B* Amplicons from 38 *Bacillus anthracis* Strains

| | 181 | 195 | 196 | 210 | 211 | 225 | 226 | 240 | |
|---|---|---|---|---|---|---|---|---|---|
| 1 Bapast | ACTGAAACAGACGTG | CATGCTGTGAAAAAA | CAAAATGCACAATCA | GCTGCAAAACAA | (SEQ ID NO: 13) |
| 2 Barec1 | ACTGAAACAGACGTG | CATGCTGTGAAAAAA | CAAAATGCACAATCA | GCTGCAAAACAA | (SEQ ID NO: 14) |
| 3 NMRI#67 | ACTGAAACAGACGTG | CATGCTGTGAAAAAA | CAAAATGCACAATCA | GCTGCAAAACAA | (SEQ ID NO: 15) |
| 4 NMRI#63 | ACTGAAACAGACGTG | CATGCTGTGAAAAAA | CAAAATGCACAATCA | GCTGCAAAACAA | (SEQ ID NO: 16) |
| 5 NMRI#62 | ACTGAAACAGACGTG | CATGCTGTGAAAAAA | CAAAATGCACAATCA | GCTGCAAAACAA | (SEQ ID NO: 17) |
| 6 NMRI#60 | ACTGAAACAGACGTG | CATGCTGTGAAAAAA | CAAAATGCACAATCA | GCTGCAAAACAA | (SEQ ID NO: 18) |
| 7 NMRI#1 | ACTGAAACAGACGTG | CATGCTGTGAAAAAA | CAAAATGCACAATCA | GCTGCAAAACAA | (SEQ ID NO: 19) |
| 8 NMRI#2 | ACTGAAACAGACGTG | CATGCTGTGAAAAAA | CAAAATGCACAATCA | GCTGCAAAACAA | (SEQ ID NO: 20) |
| 9 NMRI#4 | ACTGAAACAGACGTG | CATGCTGTGAAAAAA | CAAAATGCACAATCA | GCTGCAAAACAA | (SEQ ID NO: 21) |
| 10 NMRI#5 | ACTGAAACAGACGTG | CATGCTGTGAAAAAA | CAAAATGCACAATCA | GCTGCAAAACAA | (SEQ ID NO: 22) |
| 11 NMRI#6 | ACTGAAACAGACGTG | CATGCTGTGAAAAAA | CAAAATGCACAATCA | GCTGCAAAACAA | (SEQ ID NO: 23) |
| 12 NMRI#10 | ACTGAAACAGACGTG | CATGCTGTGAAAAAA | CAAAATGCACAATCA | GCTGCAAAACAA | (SEQ ID NO: 24) |
| 13 NMRI#11 | ACTGAAACAGACGTG | CATGCTGTGAAAAAA | CAAAATGCACAATCA | GCTGCAAAACAA | (SEQ ID NO: 25) |
| 14 NMRI#18 | ACTGAAACAGACGTG | CATGCTGTGAAAAAA | CAAAATGCACAATCA | GCTGCAAAACAA | (SEQ ID NO: 26) |
| 15 NMRI#19 | ACTGAAACAGACGTG | CATGCTGTGAAAAAA | CAAAATGCACAATCA | GCTGCAAAACAA | (SEQ ID NO: 27) |
| 16 NMRI#20 | ACTGAAACAGACGTG | CATGCTGTGAAAAAA | CAAAATGCACAATCA | GCTGCAAAACAA | (SEQ ID NO: 28) |
| 17 NMRI#22 | ACTGAAACAGACGTG | CATGCTGTGAAAAAA | CAAAATGCACAATCA | GCTGCAAAACAA | (SEQ ID NO: 29) |
| 18 NMRI#23 | ACTGAAACAGACGTG | CATGCTGTGAAAAAA | CAAAATGCACAATCA | GCTGCAAAACAA | (SEQ ID NO: 30) |
| 19 NMRI#24 | ACTGAAACAGACGTG | CATGCTGTGAAAAAA | CAAAATGCACAATCA | GCTGCAAAACAA | (SEQ ID NO: 31) |
| 20 NMRI#25 | ACTGAAACAGACGTG | CATGCTGTGAAAAAA | CAAAATGCACAATCA | GCTGCAAAACAA | (SEQ ID NO: 32) |
| 21 NMRI#26 | ACTGAAACAGACGTG | CATGCTGTGAAAAAA | CAAAATGCACAATCA | GCTGCAAAACAA | (SEQ ID NO: 33) |
| 22 NMRI#28 | ACTGAAACAGACGTG | CATGCTGTGAAAAAA | CAAAATGCACAATCA | GCTGCAAAACAA | (SEQ ID NO: 34) |
| 23 NMRI#32 | ACTGAAACAGACGTG | CATGCTGTGAAAAAA | CAAAATGCACAATCA | GCTGCAAAACAA | (SEQ ID NO: 35) |
| 24 NMRI#35 | ACTGAAACAGACGTG | CATGCTGTGAAAAAA | CAAAATGCACAATCA | GCTGCAAAACAA | (SEQ ID NO: 36) |
| 25 NMRI#36 | ACTGAAACAGACGTG | CATGCTGTGAAAAAA | CAAAATGCACAATCA | GCTGCAAAACAA | (SEQ ID NO: 37) |
| 26 NMRI#38 | ACTGAAACAGACGTG | CATGCTGTGAAAAAA | CAAAATGCACAATCA | GCTGCAAAACAA | (SEQ ID NO: 38) |
| 27 NMRI#39 | ACTGAAACAGACGTG | CATGCTGTGAAAAAA | CAAAATGCACAATCA | GCTGCAAAACAA | (SEQ ID NO: 39) |
| 28 NMRI#40 | ACTGAAACAGACGTG | CATGCTGTGAAAAAA | CAAAATGCACAATCA | GCTGCAAAACAA | (SEQ ID NO: 40) |
| 29 NMRI#41 | ACTGAAACAGACGTG | CATGCTGTGAAAAAA | CAAAATGCACAATCA | GCTGCAAAACAA | (SEQ ID NO: 41) |
| 30 NMRI#42 | ACTGAAACAGACGTG | CATGCTGTGAAAAAA | CAAAATGCACAATCA | GCTGCAAAACAA | (SEQ ID NO: 42) |
| 31 NMRI#43 | ACTGAAACAGACGTG | CATGCTGTGAAAAAA | CAAAATGCACAATCA | GCTGCAAAACAA | (SEQ ID NO: 43) |
| 32 NMRI#50 | ACTGAAACAGACGTG | CATGCTGTGAAAAAA | CAAAATGCACAATCA | GCTGCAAAACAA | (SEQ ID NO: 44) |
| 33 NMRI#52 | ACTGAAACAGACGTG | CATGCTGTGAAAAAA | CAAAATGCACAATCA | GCTGCAAAACAA | (SEQ ID NO: 45) |
| 34 NMRI#53 | ACTGAAACAGACGTG | CATGCTGTGAAAAAA | CAAAATGCACAATCA | GCTGCAAAACAA | (SEQ ID NO: 46) |
| 35 NMRI#54 | ACTGAAACAGACGTG | CATGCTGTGAAAAAA | CAAAATGCACAATCA | GCTGCAAAACAA | (SEQ ID NO: 47) |
| 36 NMRI#55 | ACTGAAACAGACGTG | CATGCTGTGAAAAAA | CAAAATGCACAATCA | GCTGCAAAACAA | (SEQ ID NO: 47) |
| 37 NMRI#56 | ACTGAAACAGACGTG | CATGCTGTGAAAAAA | CAAAATGCACAATCA | GCTGCAAAACAA | (SEQ ID NO: 49) |
| 38 NMRI#59 | ACTGAAACAGACGTG | CATGCTGTGAAAAAA | CAAAATGCACAATCA | GCTGCAAAACAA | (SEQ ID NO: 50) |

Figure 2A

Drawing ClustalW Global sasp-B DNA Sequence Alignment of *Bacillus anthracis*, *Bacillus thuringiensis* and *Bacillus cereus* Strains

| | | 1 | 15 16 | 30 31 | 45 46 | 60 61 | 75 76 | 90 |
|---|---|---|---|---|---|---|---|---|
| 1 | NMRI#15 | AACAAGGCAACTTCT | GGCGCTAGCATTCAA | AGTACAAATGCTAGT | TATGGTACAGAGTTT | TCAACTGAAACAGAT | GTGCAAGCAGTAAAA |
| 2 | 1B | AACAAGGCAACTTCT | GGCGCTAGCATTCAA | AGTACAAATGCTAGT | TATGGTACAGAGTTT | TCAACTGAAACAGAT | GTGCAAGCAGTAAAA |
| 3 | 003 | AACAAGGCAACTTCT | GGCGCTAGCATTCAA | AGTACAAATGCTAGT | TATGGTACAGAGTTT | TCAACTGAAACAGAT | GTGCAAGCAGTAAAA |
| 4 | III | AACAAGGCAACTTCT | GGCGCTAGCATTCAA | AGTACAAATGCTAGT | TATGGTACAGAGTTT | TCAACTGAAACAGAT | GTGCAAGCAGTAAAA |
| 5 | IV | AACAAGGCAACTTCT | GGCGCTAGCATTCAA | AGTACAAATGCTAGT | TATGGTACAGAGTTT | TCAACTGAAACAGAT | GTGCAAGCAGTAAAA |
| 6 | BtB | AACAAGGCAACTTCT | GGTGCTAGCATTCAA | AGTACAAATGCTAGT | TATGGTACAGAGTTT | TCAACTGAAACAGAT | GTACAAGCAGTAAAA |
| 7 | BtY | AACAAGGCAACTTCT | GGTGCTAGCATTCAA | AGTACAAATGCTAGT | TATGGTACAGAGTTT | TCAACTGAAACAGAT | GTACAAGCAGTAAAA |
| 8 | 4A1 | AACAAGGCAACTTCT | GGTGCTAGCATTCAA | AGTACAAATGCTAGT | TATGGTACAGAGTTT | GCAACTGAAACAAAT | GTACAAGCAGTAAAA |
| 9 | BtV | AACAAGGCAACTTCT | GGTGCTAGCATTCAA | AGTACAAATGCTAGT | TATGGTACAGAGTTT | GCAACTGAAACAAAT | GTACAAGCAGTAAAA |
| 10 | BtZ | AACAAGGCAACTTCT | GGTGCTAGCATTCAA | AGTACAAATGCTAGT | TATGGTACAGAGTTT | GCAACTGAAACAAAT | GTACAAGCAGTAAAA |
| 11 | Bcer3 | AACAAAGCAACTTCT | GGTGCTAGCATTCAA | AGTACAAATGCTAGT | TATGGTACAGAGTTT | TCAACTGAAACAGAT | GTACAAGCTGTAAAA |
| 12 | 1B/A | AACAAAGCAACTTCT | GGTGCTAGCATTCAA | AGTACAAATGCTAGT | TATGGTACAGAGTTT | TCAACTGAAACAGAT | GTACAAGCTGTAAAA |
| 13 | Bcerpub | AACAAAGCAACTTCT | GGTGCTAGCATTCAA | AGTACAAATGCTAGT | TATGGTACAGAGTTT | TCAACTGAAACAGAT | GTACAAGCTGTAAAA |
| 14 | BtT | AACAAAGCAACTTCT | GGTGCTAGCATTCAA | AGTACAAATGCTAGT | TATGGTACAGAGTTT | TCAACTGAAACAGAT | GTACAAGCTGTAAAA |
| 15 | BtU | AACAAAGCAACTTCT | GGTGCTAGCATTCAA | AGTACAAATGCTAGT | TATGGTACAGAGTTT | TCAACTGAAACAGAT | GTACAAGCTGTAAAA |
| 16 | BtS | AACAAAGCAACTTCT | GGTGCTAGCATTCAA | AGTACAAATGCTAGT | TATGGTACAGAGTTT | TCAACTGAAACAGAT | GTACAAGCTGTAAAA |
| 17 | BtR | AACAAGCAACTTCT | GGTGCTAGCATTCAA | AGTACAAATGCTAGT | TATGGTACAGAGTTT | TCAACTGAAACAGAT | GTACAAGCTGTAAAA |
| 18 | BtL | AACAAGGCAACTTCT | GGTGCTAGCATTCAA | AGTACAAATGCTAGT | TATGGTACAGAGTTT | TCAACTGAAACAGAT | GTACAAGCTGTAAAA |
| 19 | BtO | AACAAGGCAACTTCT | GGTGCTAGCATTCAA | AGTACAAATGCTAGT | TATGGTACAGAGTTT | TCAACTGAAACAGAT | GTACAAGCTGTAAAA |
| 20 | BtJ | AACAAGCAACTTCT | GGTGCTAGCATTCAA | AGTACAAATGCTAGT | TATGGTACAGAGTTT | TCAACTGAAACAGAT | GTACAAGCTGTAAAA |
| 21 | 4J2 | AACAAGCAACTTCT | GGTGCTAGCATTCAA | AGTACAAATGCTAGT | TATGGTACAGAGTTT | TCAACTGAAACAGAT | GTACAAGCTGTAAAA |
| 22 | BtG | AACAAGGCAACTTCT | GGTGCTAGCATTCAA | AGTACAAATGCTAGT | TATGGTACAGAGTTT | TCAACTGAAACAGAT | GTACAAGCAGTAAAA |
| 23 | BtI | AACAAGGCAACTTCT | GGTGCTAGCATTCAA | AGTACAAATGCTAGT | TATGGTACAGAGTTT | TCAACTGAAACAGAT | GTACAAGCAGTAAAA |
| 24 | Bcer2 | AACAAGGCAACTTCT | GGTGCTAGCATTCAA | AGTACAAATGCTAGT | TATGGTACAGAGTTT | TCAACTGAAACAGAT | GTACAAGCTGTAAAA |
| 25 | BtC | AACAAGGCAACTTCT | GGTGCTAGCATTCAA | AGTACAAATGCTAGT | TATGGTACAGAGTTT | GCGACTGAAACAAAT | GTACAAGCAGTAAAA |
| 26 | BtE2 | AACAAGGCAACTTCT | GGTGCTAGCATTCAA | AGTACAAATGCTAGT | TATGGTACAGAATTT | GCTACTGAAACAAAT | GTACAAGCAGTAAAA |
| 27 | BtE4 | AACAAGGCAACTTCT | GGTGCTAGCATTCAA | AGTACAAATGCTAGT | TATGGTACAGAATTT | GCTACTGAAACAAAT | GTACAAGCAGTAAAA |
| 28 | BtK | AACAAGGCAACTTCT | GGTGCTAGCATTCAA | AGTACAAATGCTAGT | TATGGTACAGAGTTT | GCGACTGAAACAAAT | GTACAAGCAGTAAAA |
| 29 | BtM | AACAAGGCAACTTCT | GGTGCTAGCATTCAA | AGTACAAATGCTAGT | TATGGTACAGAGTTT | GCGACTGAAACAAAT | GTACAAGCAGTAAAA |
| 30 | BtN | AACAAGGCAACTTCT | GGTGCTAGCATTCAA | AGTACAAATGCTAGT | TATGGTACAGAGTTT | GCGACTGAAACAAAT | GTACAAGCAGTAAAA |
| 31 | BtP | AACAAGGCAACTTCT | GGTGCTAGCATTCAA | AGTACAAATGCTAGT | TATGGTACAGAATTT | GCTACTGAAACAAAT | GTACAAGCAGTAAAA |
| 32 | BtX | AACAAGGCAACTTCT | GGTGCTAGCATTCAA | AGTACAAATGCTAGT | TATGGTACAGAATTT | GCTACTGAAACAAAT | GTACAAGCAGTAAAA |
| 33 | Bcer1 | AACAAGGCAACTTCT | GGTGCTAGCATTCAA | AGTACAAATGCTAGT | TATGGTACAGAGTTT | GCGACTGAAACAAAT | GTACAAGCAGTAAAA |
| 34 | BtQ | AACAAGGCAACTTCT | GGTGCTAGCATTCAA | AGTACAAATGCTAGT | TATGGTACAGAGTTT | GCGACTGAAACAAAT | GTACAAGCAGTAAAA |
| 35 | BtW | AACAAGGCAACTTCT | GGTGCTAGCATTCAA | AGTACAAATGCTAGT | TATGGTACAGAGTTT | GCGACTGAAACAAAT | GTACAAGCAGTAAAA |
| 36 | Bc #57 | AACAAGGCAACTTCT | GGTGCTAGCATTCAA | AGTACAAATGCTAGT | TATGGTACAGAGTTT | GCGACTGAAACAAAT | GTACAAGCAGTAAAA |
| 37 | Ba #11 | AACAAGGCAACTTCT | GGTGCTAGCATTCAA | AGCACAAATGCTAGT | TATGGTACAGAGTTT | GCGACTGAAACAAAT | GTACAAGCAGTAAAA |

Figure 2B

Drawing ClustalW Global sasp-B DNA Sequence Alignment of Bacillus anthracis,
Bacillus thuringiensis and Bacillus cereus Strains

```
        91                 105 106              120 121             135 136              150 151              165 166              180
 1 NMRI#15 CAAGCAAATGCACAA TCAGAAGCAAAGAAA GCACAAGCTTCTGGT GCA---------CAAAGT GCAAACGCTAGTTAT GGTACTGAATTTGCA
 2 1B      CAAGCAAATGCACAA TCAGAAGCAAAGAAA GCACAAGCTTCTGGT GCA---------CAAAGT GCAAACGCTAGTTAT GGTACTGAATTTGCA
 3 003     CAAGCAAATGCACAA TCAGAAGCAAAGAAA GCACAAGCTTCTGGT GCA---------CAAAGT GCAAACGCTAGTTAT GGTACTGAATTTGCA
 4 III     CAAGCAAATGCACAA TCAGAAGCAAAGAAA GCACAAGCTTCTGGT GCA---------CAAAGT GCAAACGCTAGTTAT GGTACTGAATTTGCA
 5 IV      CAAGCAAATGCACAA TCAGAAGCAAAGAAA GCACAAGCTTCTGGT GCA---------CAAAGT GCAAACGCTAGTTAT GGTACTGAATTTGCA
 6 BtB     CAAGCAAACGCACAA TCAGAAGCAAAGAAA GCACAAGCTTCTGGT GCA---------CAAAGT GCAAACGCTAGTTAT GGTACAGAATTTGCA
 7 BtY     CAAGCAAACGCACAA TCAGAAGCAAAGAAA GCACAAGCTTCTGGT GCA---------CAAAGT GCAAACGCTAGTTAT GGTACAGAATTTGCA
 8 4A1     CAAGCAAACGCACAA TCAGAAGCAAAGAAA GCACAAGCTTCTGGT GCA---------CAAAGT GCAAACGCTAGTTAT GGTACAGAATTTGCA
 9 BtV     CAAGCAAACGCACAA TCAGAAGCAAAGAAA GCACAAGCTTCTGGT GCA---------CAAAGT GCAAACGCTAGTTAT GGTACAGAATTTGCA
10 Btz     CAAGCAAACGCACAA TCAGAAGCAAAGAAA GCACAAGCTTCTGGT GCA---------CAAAGT GCAAACGCTAGTTAT GGTACAGAATTTGCA
11 Bcer3   CAAGCAAACGCACAA TCAGAAGCAAAAAAA GCACAAGCTTCTGGT GCA---------CAAAGT GCAAACGCTAGTTAT GGTACAGAATTTGCA
12 1B/A    CAAGCAAACGCACAA TCAGAAGCAAAGAAA GCACAAGCTTCTGGT GCA---------CAAAGT GCAAACGCTAGTTAT GGTACAGAATTTGCA
13 Bcerpub CAAGCAAACGCACAA TCAGAAGCAAAGAAA GCACAAGCTTCTGGT GCA---------CAAAGT GCAAACGCTAGTTAT GGTACAGAATTTGCA
14 BtT     CAAGCAAACGCACAA TCAGAAGCAAAGAAA GCACAAGCTTCTGGT GCA---------CAAAGT GCAAACGCTAGTTAT GGTACAGAATTTGCA
15 BtU     CAAGCAAACGCACAA TCAGAAGCAAAGAAA GCACAAGCTTCTGGT GCA---------CAAAGT GCAAACGCTAGTTAT GGTACAGAATTTGCA
16 BtS     CAAGCAAACGCACAA TCAGAAGCAAAGAAA GCACAAGCTTCTGGT GCA---------CAAAGT GCAAACGCTAGTTAT GGTACAGAATTTGCA
17 BtR     CAAGCAAACGCACAA TCAGAAGCAAAGAAA GCACAAGCTTCTGGT GCA---------CAAAGT GCAAACGCTAGTTAT GGTACAGAATTTGCA
18 BtL     CAAGCAAACGCACAA TCAGAAGCAAAGAAA GCACAAGCTTCTGGT GCA---------CAAAGT GCAAACGCTAGTTAT GGTACAGAATTTGCA
19 BtO     CAAGCAAACGCACAA TCAGAAGCAAAGAAA GCACAAGCTTCTGGT GCA---------CAAAGT GCAAACGCTAGTTAT GGTACAGAATTTGCA
20 BtJ     CAAGCAAACGCACAA TCAGAAGCAAAGAAA GCACAAGCTTCTGGT GCA---------CAAAGT GCAAACGCTAGTTAT GGTACAGAATTTGCA
21 4J2     CAAGCAAACGCACAA TCAGAAGCAAAGAAA GCACAAGCTTCTGGT GCA---------CAAAGT GCAAACGCTAGTTAT GGTACAGAATTTGCA
22 BtG     CAAGCAAACGCACAA TCAGAAGCAAAGAAA GCACAAGCTTCTGGT GCA---------CAAAGT GCAAACGCTAGTTAT GGTACAGAATTTGCA
23 BtI     CAAGCAAACGCACAA TCAGAAGCAAAGAAA GCACAAGCTTCTGGT GCA---------CAAAGT GCAAACGCTAGTTAT GGTACAGAATTTGCA
24 Bcer2   CAAGCAAACGCACAA TCAGAAGCAAAGAAA GCACAAGCTTCTGGT GCA---------CAAAGT GCAAACGCTAGTTAT GGTACAGAATTTGCA
25 BtC     CAAGCAAACGCACAA TCAGAAGCAAAGAAA GCACAAGCTTCTGGT GCA---------CAAAGT GCAAACGCTAGTTAT GGTACAGAATTTGCA
26 BtE2    CAAGCAAACGCACAA TCAGAAGCAAAGAAA GCACAAGCTTCTGGT GCA---------CAAAGT GCAAACGCTAGTTAT GGTACAGAATTTGCA
27 BtE4    CAAGCAAACGCACAA TCAGAAGCAAAGAAA GCACAAGCTTCTGGT GCA---------CAAAGT GCAAACGCTAGTTAT GGTACAGAATTTGCA
28 BtK     CAAGCAAACGCACAA TCAGAAGCAAAGAAA GCACAAGCTTCTGGT GCA---------CAAAGT GCAAACGCTAGTTAT GGTACAGAATTTGCA
29 BtM     CAAGCAAACGCACAA TCAGAAGCAAAGAAA GCACAAGCTTCTGGT GCA---------CAAAGT GCAAACGCTAGTTAT GGTACAGAATTTGCA
30 BtN     CAAGCAAACGCACAA TCAGAAGCAAAGAAA GCACAAGCTTCTGGT GCA---------CAAAGT GCAAACGCTAGTTAT GGTACAGAATTTGCA
31 BtP     CAAGCAAACGCACAA TCAGAAGCAAAGAAA GCACAAGCTTCTGGT GCA---------CAAAGT GCAAACGCTAGTTAT GGTACAGAATTTGCA
32 BtX     CAAGCAAACGCACAA TCAGAAGCAAAGAAA GCACAAGCTTCTGGT GCA---------CAAAGT GCAAACGCTAGTTAT GGTACAGAATTTGCA
33 Bcer1   CAAGCAAACGCACAA TCAGAAGCAAAGAAA GCACAAGCTTCTGGT GCA---------CAAAGT GCAAACGCTAGTTAT GGTACAGAATTTGCA
34 BtQ     CAAGCAAACGCACAA TCAGAAGCAAAGAAA GCACAAGCTTCTGGT GCA---------CAAAGT GCAAACGCTAGTTAT GGTACAGAATTTGCA
35 BtW     CAAGCAAACGCACAA TCAGAAGCTAAGAAA GCACAAGCTTCTGGT GCA---------CAAAGT GCAAACGCTAGTTAT GGTACAGAATTTGCA
36 NMRI#57 CAAGCAAACGCACAA TCAGAAGCAAAGAAA GCACAAGCTTCTGGT GCTAGCATTCAAAGC GCAAACGCTAGTTAT GGTACAGAATTTGCA
37 NMRI#11 CAAGCAAACGCACAA TCAGAAGCTAAGAAA GCGCAAGCTTCTGGT GCA---------CAAAGT ACAAATGCTAGTTAT GGTACAGAATTTGCA
```

Figure 2C

Drawing ClustalW Global *sasp-B* DNA Sequence Alignment of *Bacillus anthracis*, *Bacillus thuringiensis* and *Bacillus cereus* Strains

| | | 181 195 196 210 211 225 226 240 | |
|---|---|---|---|
| 1 | NMRI#15 | ACTGAAACAGAGATGTG CATGCTGTGAAAAAA CAAAATGCACAATCA GCTGCAAAACAA | (SEQ ID NO: 51) |
| 2 | 1B | ACTGAAACAGAGATGTG CATGCTGTGAAAAAA CAAAATGCACAATCA GCTGCAAAACAA | (SEQ ID NO: 52) |
| 3 | 003 | ACTGAAACAGAGATGTG CATGCTGTGAAAAAA CAAAATGCACAATCA GCTGCAAAACAA | (SEQ ID NO: 53) |
| 4 | III | ACTGAAACAGAGATGTG CATGCTGTGAAAAAA CAAAATGCACAATCA GCTGCAAAACAA | (SEQ ID NO: 54) |
| 5 | IV | ACTGAAACAGAGATGTG CATGCTGTGAAAAAA CAAAATGCACAATCA GCTGCAAAACAA | (SEQ ID NO: 55) |
| 6 | BtB | ACTGAAACAGAGACGTG CATGCTGTGAAAAAA CAAAATGCACAATCA GCTGCAAAACAA | (SEQ ID NO: 56) |
| 7 | BtY | ACTGAAACAGAGACGTG CATGCTGTGAAAAAA CAAAATGCACAATCA GCTGCAAAACAA | (SEQ ID NO: 57) |
| 8 | 4A1 | ACTGAAACAGAGACGTG CATGCTGTGAAAAAA CAAAATGCACAGTCA GCTGCAAAACAA | (SEQ ID NO: 58) |
| 9 | BtV | ACTGAAACAGAGACGTG CATGCTGTGAAAAAA CAAAATGCTAAGTCA GCTGCAAAACAA | (SEQ ID NO: 59) |
| 10 | BtZ | ACTGAAACAGAGACGTG CATGCTGTGAAAAAA CAAAATGCTAAGTCA GCTGCAAAACAA | (SEQ ID NO: 60) |
| 11 | Bcer3 | ACTGAAACAGAGACGTG CATTCTGTGAAAAAA CAAAATGCTAAGTCA GCTGCAAAACAA | (SEQ ID NO: 61) |
| 12 | 1B/A | ACTGAAACAGAGACGTG CATTCTGTGAAAAAA CAAAATGCTAAGTCA GCTGCAAAACAA | (SEQ ID NO: 62) |
| 13 | Bcerpub | ACTGAAACAGAGACGTG CATTCTGTGAAAAAA CAAAATGCTAAGTCA GCTGCAAAACAA | (SEQ ID NO: 63) |
| 14 | BtT | ACTGAAACAGAGACGTG CATTCTGTGAAAAAA CAAAATGCTAAGTCA GCTGCAAAACAA | (SEQ ID NO: 64) |
| 15 | BtU | ACTGAAACAGAGACGTG CATTCTGTGAAAAAA CAAAATGCTAAGTCA GCTGCAAAACAA | (SEQ ID NO: 65) |
| 16 | BtS | ACTGAAACAGAGACGTG CATTCTGTGAAAAAA CAAAATGCTAAGTCA GCTGCAAAACAA | (SEQ ID NO: 66) |
| 17 | BtR | ACTGAAACAGAGACGTG CATTCTGTGAAAAAA CAAAATGCTAAGTCA GCTGCAAAACAA | (SEQ ID NO: 67) |
| 18 | BtL | ACTGAAACAGAGACGTG CATGCTGTGAAAAAA CAAAATGCTAAGTCA GCTGCAAAACAA | (SEQ ID NO: 68) |
| 19 | BtO | ACTGAAACAGAGACGTG CATGCTGTGAAAAAA CAAAATGCTAAGTCA GCTGCAAAACAA | (SEQ ID NO: 69) |
| 20 | BtJ | ACTGAAACAGAGACGTG CATGCTGTGAAAAAA CAAAATGCTAAGTCA GCTGCAAAACAA | (SEQ ID NO: 70) |
| 21 | 4J2 | ACTGAAACAGAGACGTG CATGCTGTGAAAAAA CAAAATGCTAAGTCA GCTGCAAAACAA | (SEQ ID NO: 71) |
| 22 | BtG | ACTGAAACAGAGACGTG CATGCTGTGAAAAAA CAAAATGCTAAGTCA GCTGCAAAACAA | (SEQ ID NO: 72) |
| 23 | BtI | ACTGAAACAGAGACGTG CATGCTGTGAAAAAA CAAAATGCTAAGTCA GCTGCAAAACAA | (SEQ ID NO: 73) |
| 24 | Bcer2 | ACTGAAACAGAGACGTG CATGCTGTGAAAAAA CAAAATGCTAAGTCA GCTGCAAAACAA | (SEQ ID NO: 74) |
| 25 | BtC | ACTGAAACAGAGACGTG CATGCTGTGAAAAAA CAAAATGCTAAGTCA GCTGCAAAACAA | (SEQ ID NO: 75) |
| 26 | BtE2 | ACTGAAACAGAGACGTG CATGCTGTGAAAAAA CAAAATGCTAAGTCA GCTGCAAAACAA | (SEQ ID NO: 76) |
| 27 | BtE4 | ACTGAAACAGAGACGTG CATGCTGTGAAAAAA CAAAATGCTAAGTCA GCTGCAAAACAA | (SEQ ID NO: 77) |
| 28 | BtK | ACTGAAACAGAGACGTG CATGCTGTGAAAAAA CAAAATGCTAAGTCA GCTGCAAAACAA | (SEQ ID NO: 78) |
| 29 | BtM | ACTGAAACAGAGACGTG CATGCTGTGAAAAAA CAAAATGCTAAGTCA GCTGCAAAACAA | (SEQ ID NO: 79) |
| 30 | BtN | ACTGAAACAGAGACGTG CATGCTGTGAAAAAA CAAAATGCTAAGTCA GCTGCAAAACAA | (SEQ ID NO: 80) |
| 31 | BtP | ACTGAAACAGAGACGTG CATGCTGTGAAAAAA CAAAATGCTAAGTCA GCTGCAAAACAA | (SEQ ID NO: 81) |
| 32 | BtX | ACTGAAACAGAGACGTG CATGCTGTGAAAAAA CAAAATGCTAAGTCA GCTGCAAAACAA | (SEQ ID NO: 82) |
| 33 | Bcer1 | ACTGAAACAGAGACGTG CATGCTGTGAAAAAA CAAAATGCTAAGTCA GCTGCAAAACAA | (SEQ ID NO: 83) |
| 34 | BtQ | ACTGAAACAGAGACGTG CATGCTGTGAAAAAA CAAAATGCTAAGTCA GCTGCAAAACAA | (SEQ ID NO: 84) |
| 35 | BtW | ACTGAAACAGAGACGTG CATGCTGTGAAAAAA CAAAATGCTAAGTCA GCTGCAAAACAA | (SEQ ID NO: 85) |
| 36 | NMRI#57 | ACTGAAACAGAGACGTG CATGCTGTGAAAAAA CAAAATGCACAATCA GCTGCAAAACAA | (SEQ ID NO: 86) |
| 37 | NMRI#11 | ACTGAAACAGAGACGTG CATGCTGTGAAAAAA CAAAATGCACAATCA GCTGCAAAACAA | (SEQ ID NO: 87) |

Figure 3
Bacillus globigii specific PCR targeting Bg sasp-gamma

```
                 1              15 16                         30 31                         45 46                         60 61                         75 76                         90
BgSSPE_edited_   -------------------------------------------------------------------------------------------------------------ATTCTA AT CGTGGAGGTG
Bs_pub_SSPE      TTGACGCGGACGCTC ACTGCTCGTTAAAA ATTTTTAAAAAAGAG GAATAGCTATACGAT CACCTGCACATTCTA AT CGTGGAGGTG Forward primer (BgSaspGam 5')
                 91             105 106                       120 121                       135 136                       150 151                       165 166                       180
BgSSPE_edited_   ATAA ATGGCTAAC TCAAA AAC AAACAAAACGCTCAA CAAGT AGAAAAACAA AACCAACAATCAGCA CTGG CAAGGTCA
Bs_pub_SSPE      ATAA ATGGCTAAC TCAAA AAC AAACAAAACGCTCAA CAAGT AGAAAAACAA AACCAACAATCAGCT CTGG CAAGGTCA Reverse primer (BgSaspGam 3')
                 181            195 196                       210 211                       225 226                       240 241                       255 256                       270
BgSSPE_edited_   TTTGGTAC GAATTT GCTAGCGAAACAAAC G CAACAAGT AGA AAACAAAACCAACAA TCAGCTGCTGGACAA GG CAATTCGGCACT
Bs_pub_SSPE      TTTGGCAC GAATTT GCTAGCGAAACAAAC G CAGCAAGT AGA AAACAAAACCAGCAA TCAGCTGGACAACAA GG CAATTCGGCACT 271            285 286                       300 301                       315 316                       330 331                       345 346                       360
BgSSPE_edited_   GAATTCGCTAGTGAA ACTGATGCTCAGCA GTAAGACAGCAAAAC CAATCTGCTGAACAA AACAACAACAACAAAAC AGCTAATCACTGAAA
Bs_pub_SSPE      GAATTCGCTAGTGAA ACTGACGCGCACAGCA GTAAGACAGCAAAAC CAATCTCCTGAACAA AACAACAACAACAAAAC AGCTAATCACTGAAA 361            375 376                       390 391                       405 406                       420 421                       435 436                       450
BgSSPE_edited_   CAGAAAAAAA GCACT TCATC TCGGGTGGA AGTGCTTTTTTCTTT TTATAAACGACAAA ACTTGTGGAA                                              355
Bs_pub_SSPE      CAGAAAAAAA GCACT TCATC TCGG--------------------------------------------------------                                    384

BgSSPE_edited   SEQ ID NO: 110
Bs_pub_SSPE     SEQ ID NO: 111
```

SEQUENCE LISTING

<160> NUMBER OF SEQ ID NOS: 112

<210> SEQ ID NO 1
<211> LENGTH: 24
<212> TYPE: DNA
<213> ORGANISM: Bacillus cereus

<400> SEQUENCE: 1
atgagtaaaa aacaacaagg ttat                                      24

<210> SEQ ID NO 2
<211> LENGTH: 24
<212> TYPE: DNA
<213> ORGANISM: Bacillus cereus

<400> SEQUENCE: 2
agtgttagaa gatcgagttt agtc                                      24

<210> SEQ ID NO 3
<211> LENGTH: 24
<212> TYPE: DNA
<213> ORGANISM: Bacillus cereus

<400> SEQUENCE: 3
atgggaaaaa ataatagtgg aagt                                      24

<210> SEQ ID NO 4
<211> LENGTH: 22
<212> TYPE: DNA
<213> ORGANISM: Bacillus cereus

<400> SEQUENCE: 4
tgaaccacca tctcgattgg cg                                        22

<210> SEQ ID NO 5
<211> LENGTH: 23
<212> TYPE: DNA
<213> ORGANISM: Bacillus cereus

<400> SEQUENCE: 5
atgtcagcta gcacaaataa att                                       23

<210> SEQ ID NO 6
<211> LENGTH: 21
<212> TYPE: DNA
<213> ORGANISM: Bacillus cereus

<400> SEQUENCE: 6
aatccgccaa tggttttat t                                          21

<210> SEQ ID NO 7
<211> LENGTH: 161
<212> TYPE: DNA

<213> ORGANISM: Bacillus cereus

<400> SEQUENCE: 7

| cgtaatgaag | tattagttcg | aggcgctgaa | caagctcttg | atcaaatgaa | atatgaaatt | 60 |
| gcacaagagt | ttggtgtaca | acttggtgca | gatacaacag | ctcgttcaaa | cggatctgtt | 120 |
| ggtggtgaaa | ttacaaaacg | tttagtagca | atggcagaac | a | | 161 |

<210> SEQ ID NO 8
<211> LENGTH: 161
<212> TYPE: DNA
<213> ORGANISM: Bacillus anthracis

<400> SEQUENCE: 8

| cgtaatgaat | tattagttcg | aggtgctgaa | caagctcttg | atcaaatgaa | atatgaaatt | 60 |
| gcacaagagt | ttggtgtaca | acttggtgca | gatacaacag | ctcgttcaaa | tggatctgtt | 120 |
| ggtggtgaaa | ttacaaaacg | tttagtagca | atggctgaac | a | | 161 |

<210> SEQ ID NO 9
<211> LENGTH: 154
<212> TYPE: DNA
<213> ORGANISM: Bacillus cereus

<400> SEQUENCE: 9

| agcggttcct | ggtgctgaat | cagcattaga | ccaaatgaaa | tacgaaatcg | ctcaagagtt | 60 |
| tggtgttcaa | cttggagctg | atgcaacagc | tcgcgctaac | ggttctgttg | gtggcgaaat | 120 |
| cactaaacgt | ctagtttcac | tagctgagca | acaa | | | 154 |

<210> SEQ ID NO 10
<211> LENGTH: 154
<212> TYPE: DNA
<213> ORGANISM: Bacillus anthracis

<400> SEQUENCE: 10

| agcggttcct | ggtgctgaat | cagcattaga | ccaaatgaaa | tacgaaatcg | ctcaagagtt | 60 |
| tggtgttcaa | cttggagctg | atgcaacagc | tcgcgctaac | ggttctgttg | gtggcgaaat | 120 |
| cactaaacgt | ctagtttcac | tagctgagca | acaa | | | 154 |

<210> SEQ ID NO 11
<211> LENGTH: 231
<212> TYPE: DNA
<213> ORGANISM: Bacillus cereus

<400> SEQUENCE: 11

| aacaaagcaa | cttctggtgc | tagcattcaa | agtacaaatg | ctagttatgg | tacagagttt | 60 |
| tcaactgaaa | cagatgtaca | agctgtaaaa | caagcaaacg | cacaatcaga | agcaaagaaa | 120 |
| gcacaagctt | ctggtgcaca | aagtgcaaac | gctagttatg | gtacagaatt | tgcaactgaa | 180 |
| acagacgtgc | attctgtgaa | aaacaaaat | gctaagtcag | ctgcaaaaca | a | 231 |

<210> SEQ ID NO 12
<211> LENGTH: 237
<212> TYPE: DNA
<213> ORGANISM: Bacillus anthracis

<400> SEQUENCE: 12

| aacaaggcaa | cttctggtgc | tagcattcaa | agcacaaatg | ctagttatgg | tacagagttt | 60 |
| gcgactgaaa | caaatgtaca | agcagtaaaa | caagcaaacg | cacaatcaga | agctaagaaa | 120 |

```
gcgcaagctt ctggtgctag cattcaaagc acaaatgcta gttatggtac agaatttgca      180
actgaaacag acgtgcatgc tgtgaaaaaa caaaatgcac aatcagctgc aaaacaa         237

<210> SEQ ID NO 13
<211> LENGTH: 237
<212> TYPE: DNA
<213> ORGANISM: Bacillus anthracis

<400> SEQUENCE: 13
aacaaggcaa cttctggtgc tagcattcaa agcacaaatg ctagttatgg tacagagttt      60
gcgactgaaa caaatgtaca agcagtaaaa caagcaaacg cacaatcaga agctaagaaa     120
gcgcaagctt ctggtgctag cattcaaagc acaaatgcta gttatggtac agaatttgca    180
actgaaacag acgtgcatgc tgtgaaaaaa caaaatgcac aatcagctgc aaaacaa       237

<210> SEQ ID NO 14
<211> LENGTH: 237
<212> TYPE: DNA
<213> ORGANISM: Bacillus anthracis

<400> SEQUENCE: 14
aacaaggcaa cttctggtgc tagcattcaa agcacaaatg ctagttatgg tacagagttt      60
gcgactgaaa caaatgtaca agcagtaaaa caagcaaacg cacaatcaga agctaagaaa     120
gcgcaagctt ctggtgctag cattcaaagc acaaatgcta gttatggtac agaatttgca    180
actgaaacag acgtgcatgc tgtgaaaaaa caaaatgcac aatcagctgc aaaacaa       237

<210> SEQ ID NO 15
<211> LENGTH: 237
<212> TYPE: DNA
<213> ORGANISM: Bacillus anthracis

<400> SEQUENCE: 15
aacaaggcaa cttctggtgc tagcattcaa agcacaaatg ctagttatgg tacagagttt      60
gcgactgaaa caaatgtaca agcagtaaaa caagcaaacg cacaatcaga agctaagaaa     120
gcgcaagctt ctggtgctag cattcaaagc acaaatgcta gttatggtac agaatttgca    180
actgaaacag acgtgcatgc tgtgaaaaaa caaaatgcac aatcagctgc aaaacaa       237

<210> SEQ ID NO 16
<211> LENGTH: 237
<212> TYPE: DNA
<213> ORGANISM: Bacillus anthracis

<400> SEQUENCE: 16
aacaaggcaa cttctggtgc tagcattcaa agcacaaatg ctagttatgg tacagagttt      60
gcgactgaaa caaatgtaca agcagtaaaa caagcaaacg cacaatcaga agctaagaaa     120
gcgcaagctt ctggtgctag cattcaaagc acaaatgcta gttatggtac agaatttgca    180
actgaaacag acgtgcatgc tgtgaaaaaa caaaatgcac aatcagctgc aaaacaa       237

<210> SEQ ID NO 17
<211> LENGTH: 237
<212> TYPE: DNA
<213> ORGANISM: Bacillus anthracis

<400> SEQUENCE: 17
aacaaggcaa cttctggtgc tagcattcaa agcacaaatg ctagttatgg tacagagttt      60
```

```
gcgactgaaa caaatgtaca agcagtaaaa caagcaaacg cacaatcaga agctaagaaa      120
gcgcaagctt ctggtgctag cattcaaagc acaaatgcta gttatggtac agaatttgca      180
actgaaacag acgtgcatgc tgtgaaaaaa caaaatgcac aatcagctgc aaaacaa         237

<210> SEQ ID NO 18
<211> LENGTH: 237
<212> TYPE: DNA
<213> ORGANISM: Bacillus anthracis

<400> SEQUENCE: 18
aacaaggcaa cttctggtgc tagcattcaa agcacaaatg ctagttatgg tacagagttt       60
gcgactgaaa caaatgtaca agcagtaaaa caagcaaacg cacaatcaga agctaagaaa      120
gcgcaagctt ctggtgctag cattcaaagc acaaatgcta gttatggtac agaatttgca      180
actgaaacag acgtgcatgc tgtgaaaaaa caaaatgcac aatcagctgc aaaacaa         237

<210> SEQ ID NO 19
<211> LENGTH: 237
<212> TYPE: DNA
<213> ORGANISM: Bacillus anthracis

<400> SEQUENCE: 19
aacaaggcaa cttctggtgc tagcattcaa agcacaaatg ctagttatgg tacagagttt       60
gcgactgaaa caaatgtaca agcagtaaaa caagcaaacg cacaatcaga agctaagaaa      120
gcgcaagctt ctggtgctag cattcaaagc acaaatgcta gttatggtac agaatttgca      180
actgaaacag acgtgcatgc tgtgaaaaaa caaaatgcac aatcagctgc aaaacaa         237

<210> SEQ ID NO 20
<211> LENGTH: 237
<212> TYPE: DNA
<213> ORGANISM: Bacillus anthracis

<400> SEQUENCE: 20
aacaaggcaa cttctggtgc tagcattcaa agcacaaatg ctagttatgg tacagagttt       60
gcgactgaaa caaatgtaca agcagtaaaa caagcaaacg cacaatcaga agctaagaaa      120
gcgcaagctt ctggtgctag cattcaaagc acaaatgcta gttatggtac agaatttgca      180
actgaaacag acgtgcatgc tgtgaaaaaa caaaatgcac aatcagctgc aaaacaa         237

<210> SEQ ID NO 21
<211> LENGTH: 237
<212> TYPE: DNA
<213> ORGANISM: Bacillus anthracis

<400> SEQUENCE: 21
aacaaggcaa cttctggtgc tagcattcaa agcacaaatg ctagttatgg tacagagttt       60
gcgactgaaa caaatgtaca agcagtaaaa caagcaaacg cacaatcaga agctaagaaa      120
gcgcaagctt ctggtgctag cattcaaagc acaaatgcta gttatggtac agaatttgca      180
actgaaacag acgtgcatgc tgtgaaaaaa caaaatgcac aatcagctgc aaaacaa         237

<210> SEQ ID NO 22
<211> LENGTH: 237
<212> TYPE: DNA
<213> ORGANISM: Bacillus anthracis

<400> SEQUENCE: 22
aacaaggcaa cttctggtgc tagcattcaa agcacaaatg ctagttatgg tacagagttt       60
```

```
gcgactgaaa caaatgtaca agcagtaaaa caagcaaacg cacaatcaga agctaagaaa      120
gcgcaagctt ctggtgctag cattcaaagc acaaatgcta gttatggtac agaatttgca      180
actgaaacag acgtgcatgc tgtgaaaaaa caaaatgcac aatcagctgc aaaacaa         237

<210> SEQ ID NO 23
<211> LENGTH: 237
<212> TYPE: DNA
<213> ORGANISM: Bacillus anthracis

<400> SEQUENCE: 23
aacaaggcaa cttctggtgc tagcattcaa agcacaaatg ctagttatgg tacagagttt       60
gcgactgaaa caaatgtaca agcagtaaaa caagcaaacg cacaatcaga agctaagaaa      120
gcgcaagctt ctggtgctag cattcaaagc acaaatgcta gttatggtac agaatttgca      180
actgaaacag acgtgcatgc tgtgaaaaaa caaaatgcac aatcagctgc aaaacaa         237

<210> SEQ ID NO 24
<211> LENGTH: 237
<212> TYPE: DNA
<213> ORGANISM: Bacillus anthracis

<400> SEQUENCE: 24
aacaaggcaa cttctggtgc tagcattcaa agcacaaatg ctagttatgg tacagagttt       60
gcgactgaaa caaatgtaca agcagtaaaa caagcaaacg cacaatcaga agctaagaaa      120
gcgcaagctt ctggtgctag cattcaaagc acaaatgcta gttatggtac agaatttgca      180
actgaaacag acgtgcatgc tgtgaaaaaa caaaatgcac aatcagctgc aaaacaa         237

<210> SEQ ID NO 25
<211> LENGTH: 237
<212> TYPE: DNA
<213> ORGANISM: Bacillus anthracis

<400> SEQUENCE: 25
aacaaggcaa cttctggtgc tagcattcaa agcacaaatg ctagttatgg tacagagttt       60
gcgactgaaa caaatgtaca agcagtaaaa caagcaaacg cacaatcaga agctaagaaa      120
gcgcaagctt ctggtgctag cattcaaagc acaaatgcta gttatggtac agaatttgca      180
actgaaacag acgtgcatgc tgtgaaaaaa caaaatgcac aatcagctgc aaaacaa         237

<210> SEQ ID NO 26
<211> LENGTH: 237
<212> TYPE: DNA
<213> ORGANISM: Bacillus anthracis

<400> SEQUENCE: 26
aacaaggcaa cttctggtgc tagcattcaa agcacaaatg ctagttatgg tacagagttt       60
gcgactgaaa caaatgtaca agcagtaaaa caagcaaacg cacaatcaga agctaagaaa      120
gcgcaagctt ctggtgctag cattcaaagc acaaatgcta gttatggtac agaatttgca      180
actgaaacag acgtgcatgc tgtgaaaaaa caaaatgcac aatcagctgc aaaacaa         237

<210> SEQ ID NO 27
<211> LENGTH: 237
<212> TYPE: DNA
<213> ORGANISM: Bacillus anthracis

<400> SEQUENCE: 27
```

-continued

| | |
|---|---|
| aacaaggcaa cttctggtgc tagcattcaa agcacaaatg ctagttatgg tacagagttt | 60 |
| gcgactgaaa caaatgtaca agcagtaaaa caagcaaacg cacaatcaga agctaagaaa | 120 |
| gcgcaagctt ctggtgctag cattcaaagc acaaatgcta gttatggtac agaatttgca | 180 |
| actgaaacag acgtgcatgc tgtgaaaaaa caaaatgcac aatcagctgc aaaacaa | 237 |

<210> SEQ ID NO 28
<211> LENGTH: 237
<212> TYPE: DNA
<213> ORGANISM: Bacillus anthracis

<400> SEQUENCE: 28

| | |
|---|---|
| aacaaggcaa cttctggtgc tagcattcaa agcacaaatg ctagttatgg tacagagttt | 60 |
| gcgactgaaa caaatgtaca agcagtaaaa caagcaaacg cacaatcaga agctaagaaa | 120 |
| gcgcaagctt ctggtgctag cattcaaagc acaaatgcta gttatggtac agaatttgca | 180 |
| actgaaacag acgtgcatgc tgtgaaaaaa caaaatgcac aatcagctgc aaaacaa | 237 |

<210> SEQ ID NO 29
<211> LENGTH: 237
<212> TYPE: DNA
<213> ORGANISM: Bacillus anthracis

<400> SEQUENCE: 29

| | |
|---|---|
| aacaaggcaa cttctggtgc tagcattcaa agcacaaatg ctagttatgg tacagagttt | 60 |
| gcgactgaaa caaatgtaca agcagtaaaa caagcaaacg cacaatcaga agctaagaaa | 120 |
| gcgcaagctt ctggtgctag cattcaaagc acaaatgcta gttatggtac agaatttgca | 180 |
| actgaaacag acgtgcatgc tgtgaaaaaa caaaatgcac aatcagctgc aaaacaa | 237 |

<210> SEQ ID NO 30
<211> LENGTH: 237
<212> TYPE: DNA
<213> ORGANISM: Bacillus anthracis

<400> SEQUENCE: 30

| | |
|---|---|
| aacaaggcaa cttctggtgc tagcattcaa agcacaaatg ctagttatgg tacagagttt | 60 |
| gcgactgaaa caaatgtaca agcagtaaaa caagcaaacg cacaatcaga agctaagaaa | 120 |
| gcgcaagctt ctggtgctag cattcaaagc acaaatgcta gttatggtac agaatttgca | 180 |
| actgaaacag acgtgcatgc tgtgaaaaaa caaaatgcac aatcagctgc aaaacaa | 237 |

<210> SEQ ID NO 31
<211> LENGTH: 237
<212> TYPE: DNA
<213> ORGANISM: Bacillus anthracis

<400> SEQUENCE: 31

| | |
|---|---|
| aacaaggcaa cttctggtgc tagcattcaa agcacaaatg ctagttatgg tacagagttt | 60 |
| gcgactgaaa caaatgtaca agcagtaaaa caagcaaacg cacaatcaga agctaagaaa | 120 |
| gcgcaagctt ctggtgctag cattcaaagc acaaatgcta gttatggtac agaatttgca | 180 |
| actgaaacag acgtgcatgc tgtgaaaaaa caaaatgcac aatcagctgc aaaacaa | 237 |

<210> SEQ ID NO 32
<211> LENGTH: 237
<212> TYPE: DNA
<213> ORGANISM: Bacillus anthracis

<400> SEQUENCE: 32

```
aacaaggcaa cttctggtgc tagcattcaa agcacaaatg ctagttatgg tacagagttt      60
gcgactgaaa caaatgtaca agcagtaaaa caagcaaacg cacaatcaga agctaagaaa     120
gcgcaagctt ctggtgctag cattcaaagc acaaatgcta gttatggtac agaatttgca     180
actgaaacag acgtgcatgc tgtgaaaaaa caaaatgcac aatcagctgc aaaacaa       237
```

<210> SEQ ID NO 33
<211> LENGTH: 237
<212> TYPE: DNA
<213> ORGANISM: Bacillus anthracis

<400> SEQUENCE: 33

```
aacaaggcaa cttctggtgc tagcattcaa agcacaaatg ctagttatgg tacagagttt      60
gcgactgaaa caaatgtaca agcagtaaaa caagcaaacg cacaatcaga agctaagaaa     120
gcgcaagctt ctggtgctag cattcaaagc acaaatgcta gttatggtac agaatttgca     180
actgaaacag acgtgcatgc tgtgaaaaaa caaaatgcac aatcagctgc aaaacaa       237
```

<210> SEQ ID NO 34
<211> LENGTH: 237
<212> TYPE: DNA
<213> ORGANISM: Bacillus anthracis

<400> SEQUENCE: 34

```
aacaaggcaa cttctggtgc tagcattcaa agcacaaatg ctagttatgg tacagagttt      60
gcgactgaaa caaatgtaca agcagtaaaa caagcaaacg cacaatcaga agctaagaaa     120
gcgcaagctt ctggtgctag cattcaaagc acaaatgcta gttatggtac agaatttgca     180
actgaaacag acgtgcatgc tgtgaaaaaa caaaatgcac aatcagctgc aaaacaa       237
```

<210> SEQ ID NO 35
<211> LENGTH: 237
<212> TYPE: DNA
<213> ORGANISM: Bacillus anthracis

<400> SEQUENCE: 35

```
aacaaggcaa cttctggtgc tagcattcaa agcacaaatg ctagttatgg tacagagttt      60
gcgactgaaa caaatgtaca agcagtaaaa caagcaaacg cacaatcaga agctaagaaa     120
gcgcaagctt ctggtgctag cattcaaagc acaaatgcta gttatggtac agaatttgca     180
actgaaacag acgtgcatgc tgtgaaaaaa caaaatgcac aatcagctgc aaaacaa       237
```

<210> SEQ ID NO 36
<211> LENGTH: 237
<212> TYPE: DNA
<213> ORGANISM: Bacillus anthracis

<400> SEQUENCE: 36

```
aacaaggcaa cttctggtgc tagcattcaa agcacaaatg ctagttatgg tacagagttt      60
gcgactgaaa caaatgtaca agcagtaaaa caagcaaacg cacaatcaga agctaagaaa     120
gcgcaagctt ctggtgctag cattcaaagc acaaatgcta gttatggtac agaatttgca     180
actgaaacag acgtgcatgc tgtgaaaaaa caaaatgcac aatcagctgc aaaacaa       237
```

<210> SEQ ID NO 37
<211> LENGTH: 237
<212> TYPE: DNA
<213> ORGANISM: Bacillus anthracis

<400> SEQUENCE: 37

```
aacaaggcaa cttctggtgc tagcattcaa agcacaaatg ctagttatgg tacagagttt      60
gcgactgaaa caaatgtaca agcagtaaaa caagcaaacg cacaatcaga agctaagaaa     120
gcgcaagctt ctggtgctag cattcaaagc acaaatgcta gttatggtac agaatttgca     180
actgaaacag acgtgcatgc tgtgaaaaaa caaaatgcac aatcagctgc aaaacaa       237
```

<210> SEQ ID NO 38
<211> LENGTH: 237
<212> TYPE: DNA
<213> ORGANISM: Bacillus anthracis

<400> SEQUENCE: 38

```
aacaaggcaa cttctggtgc tagcattcaa agcacaaatg ctagttatgg tacagagttt      60
gcgactgaaa caaatgtaca agcagtaaaa caagcaaacg cacaatcaga agctaagaaa     120
gcgcaagctt ctggtgctag cattcaaagc acaaatgcta gttatggtac agaatttgca     180
actgaaacag acgtgcatgc tgtgaaaaaa caaaatgcac aatcagctgc aaaacaa       237
```

<210> SEQ ID NO 39
<211> LENGTH: 237
<212> TYPE: DNA
<213> ORGANISM: Bacillus anthracis

<400> SEQUENCE: 39

```
aacaaggcaa cttctggtgc tagcattcaa agcacaaatg ctagttatgg tacagagttt      60
gcgactgaaa caaatgtaca agcagtaaaa caagcaaacg cacaatcaga agctaagaaa     120
gcgcaagctt ctggtgctag cattcaaagc acaaatgcta gttatggtac agaatttgca     180
actgaaacag acgtgcatgc tgtgaaaaaa caaaatgcac aatcagctgc aaaacaa       237
```

<210> SEQ ID NO 40
<211> LENGTH: 237
<212> TYPE: DNA
<213> ORGANISM: Bacillus anthracis

<400> SEQUENCE: 40

```
aacaaggcaa cttctggtgc tagcattcaa agcacaaatg ctagttatgg tacagagttt      60
gcgactgaaa caaatgtaca agcagtaaaa caagcaaacg cacaatcaga agctaagaaa     120
gcgcaagctt ctggtgctag cattcaaagc acaaatgcta gttatggtac agaatttgca     180
actgaaacag acgtgcatgc tgtgaaaaaa caaaatgcac aatcagctgc aaaacaa       237
```

<210> SEQ ID NO 41
<211> LENGTH: 237
<212> TYPE: DNA
<213> ORGANISM: Bacillus anthracis

<400> SEQUENCE: 41

```
aacaaggcaa cttctggtgc tagcattcaa agcacaaatg ctagttatgg tacagagttt      60
gcgactgaaa caaatgtaca agcagtaaaa caagcaaacg cacaatcaga agctaagaaa     120
gcgcaagctt ctggtgctag cattcaaagc acaaatgcta gttatggtac agaatttgca     180
actgaaacag acgtgcatgc tgtgaaaaaa caaaatgcac aatcagctgc aaaacaa       237
```

<210> SEQ ID NO 42
<211> LENGTH: 237
<212> TYPE: DNA
<213> ORGANISM: Bacillus anthracis

<400> SEQUENCE: 42
aacaaggcaa cttctggtgc tagcattcaa agcacaaatg ctagttatgg tacagagttt      60
gcgactgaaa caaatgtaca agcagtaaaa caagcaaacg cacaatcaga agctaagaaa     120
gcgcaagctt ctggtgctag cattcaaagc acaaatgcta gttatggtac agaatttgca     180
actgaaacag acgtgcatgc tgtgaaaaaa caaaatgcac aatcagctgc aaaacaa       237

<210> SEQ ID NO 43
<211> LENGTH: 237
<212> TYPE: DNA
<213> ORGANISM: Bacillus anthracis

<400> SEQUENCE: 43
aacaaggcaa cttctggtgc tagcattcaa agcacaaatg ctagttatgg tacagagttt      60
gcgactgaaa caaatgtaca agcagtaaaa caagcaaacg cacaatcaga agctaagaaa     120
gcgcaagctt ctggtgctag cattcaaagc acaaatgcta gttatggtac agaatttgca     180
actgaaacag acgtgcatgc tgtgaaaaaa caaaatgcac aatcagctgc aaaacaa       237

<210> SEQ ID NO 44
<211> LENGTH: 237
<212> TYPE: DNA
<213> ORGANISM: Bacillus anthracis

<400> SEQUENCE: 44
aacaaggcaa cttctggtgc tagcattcaa agcacaaatg ctagttatgg tacagagttt      60
gcgactgaaa caaatgtaca agcagtaaaa caagcaaacg cacaatcaga agctaagaaa     120
gcgcaagctt ctggtgctag cattcaaagc acaaatgcta gttatggtac agaatttgca     180
actgaaacag acgtgcatgc tgtgaaaaaa caaaatgcac aatcagctgc aaaacaa       237

<210> SEQ ID NO 45
<211> LENGTH: 237
<212> TYPE: DNA
<213> ORGANISM: Bacillus anthracis

<400> SEQUENCE: 45
aacaaggcaa cttctggtgc tagcattcaa agcacaaatg ctagttatgg tacagagttt      60
gcgactgaaa caaatgtaca agcagtaaaa caagcaaacg cacaatcaga agctaagaaa     120
gcgcaagctt ctggtgctag cattcaaagc acaaatgcta gttatggtac agaatttgca     180
actgaaacag acgtgcatgc tgtgaaaaaa caaaatgcac aatcagctgc aaaacaa       237

<210> SEQ ID NO 46
<211> LENGTH: 237
<212> TYPE: DNA
<213> ORGANISM: Bacillus anthracis

<400> SEQUENCE: 46
aacaaggcaa cttctggtgc tagcattcaa agcacaaatg ctagttatgg tacagagttt      60
gcgactgaaa caaatgtaca agcagtaaaa caagcaaacg cacaatcaga agctaagaaa     120
gcgcaagctt ctggtgctag cattcaaagc acaaatgcta gttatggtac agaatttgca     180
actgaaacag acgtgcatgc tgtgaaaaaa caaaatgcac aatcagctgc aaaacaa       237

<210> SEQ ID NO 47
<211> LENGTH: 237
<212> TYPE: DNA

<213> ORGANISM: Bacillus anthracis

<400> SEQUENCE: 47

| aacaaggcaa cttctggtgc tagcattcaa agcacaaatg ctagttatgg tacagagttt | 60 |
| gcgactgaaa caaatgtaca agcagtaaaa caagcaaacg cacaatcaga agctaagaaa | 120 |
| gcgcaagctt ctggtgctag cattcaaagc acaaatgcta gttatggtac agaatttgca | 180 |
| actgaaacag acgtgcatgc tgtgaaaaaa caaaatgcac aatcagctgc aaaacaa | 237 |

<210> SEQ ID NO 48
<211> LENGTH: 237
<212> TYPE: DNA
<213> ORGANISM: Bacillus anthracis

<400> SEQUENCE: 48

| aacaaggcaa cttctggtgc tagcattcaa agcacaaatg ctagttatgg tacagagttt | 60 |
| gcgactgaaa caaatgtaca agcagtaaaa caagcaaacg cacaatcaga agctaagaaa | 120 |
| gcgcaagctt ctggtgctag cattcaaagc acaaatgcta gttatggtac agaatttgca | 180 |
| actgaaacag acgtgcatgc tgtgaaaaaa caaaatgcac aatcagctgc aaaacaa | 237 |

<210> SEQ ID NO 49
<211> LENGTH: 237
<212> TYPE: DNA
<213> ORGANISM: Bacillus anthracis

<400> SEQUENCE: 49

| aacaaggcaa cttctggtgc tagcattcaa agcacaaatg ctagttatgg tacagagttt | 60 |
| gcgactgaaa caaatgtaca agcagtaaaa caagcaaacg cacaatcaga agctaagaaa | 120 |
| gcgcaagctt ctggtgctag cattcaaagc acaaatgcta gttatggtac agaatttgca | 180 |
| actgaaacag acgtgcatgc tgtgaaaaaa caaaatgcac aatcagctgc aaaacaa | 237 |

<210> SEQ ID NO 50
<211> LENGTH: 237
<212> TYPE: DNA
<213> ORGANISM: Bacillus anthracis

<400> SEQUENCE: 50

| aacaaggcaa cttctggtgc tagcattcaa agcacaaatg ctagttatgg tacagagttt | 60 |
| gcgactgaaa caaatgtaca agcagtaaaa caagcaaacg cacaatcaga agctaagaaa | 120 |
| gcgcaagctt ctggtgctag cattcaaagc acaaatgcta gttatggtac agaatttgca | 180 |
| actgaaacag acgtgcatgc tgtgaaaaaa caaaatgcac aatcagctgc aaaacaa | 237 |

<210> SEQ ID NO 51
<211> LENGTH: 231
<212> TYPE: DNA
<213> ORGANISM: Bacillus anthracis

<400> SEQUENCE: 51

| aacaaggcaa cttctggcgc tagcattcaa agtacaaatg ctagttatgg tacagagttt | 60 |
| tcaactgaaa cagatgtgca agcagtaaaa caagcaaatg cacaatcaga agcaaagaaa | 120 |
| gcacaagctt ctggtgcaca aagtgcaaac gctagttatg gtactgaatt tgcaactgaa | 180 |
| acagatgtgc atgctgtgaa aaaacaaaat gcacaatcag ctgcaaaaca a | 231 |

<210> SEQ ID NO 52
<211> LENGTH: 231

-continued

<212> TYPE: DNA
<213> ORGANISM: Unidentified Bacillus

<400> SEQUENCE: 52
aacaaggcaa cttctggcgc tagcattcaa agtacaaatg ctagttatgg tacagagttt 60
tcaactgaaa cagatgtgca agcagtaaaa caagcaaatg cacaatcaga agcaaagaaa 120
gcacaagctt ctggtgcaca aagtgcaaac gctagttatg gtactgaatt tgcaactgaa 180
acagatgtgc atgctgtgaa aaaacaaaat gcacaatcag ctgcaaaaca a 231

<210> SEQ ID NO 53
<211> LENGTH: 231
<212> TYPE: DNA
<213> ORGANISM: Unidentified Bacillus

<400> SEQUENCE: 53
aacaaggcaa cttctggcgc tagcattcaa agtacaaatg ctagttatgg tacagagttt 60
tcaactgaaa cagatgtgca agcagtaaaa caagcaaatg cacaatcaga agcaaagaaa 120
gcacaagctt ctggtgcaca aagtgcaaac gctagttatg gtactgaatt tgcaactgaa 180
acagatgtgc atgctgtgaa aaaacaaaat gcacaatcag ctgcaaaaca a 231

<210> SEQ ID NO 54
<211> LENGTH: 231
<212> TYPE: DNA
<213> ORGANISM: Unidentified Bacillus

<400> SEQUENCE: 54
aacaaggcaa cttctggcgc tagcattcaa agtacaaatg ctagttatgg tacagagttt 60
tcaactgaaa cagatgtgca agcagtaaaa caagcaaatg cacaatcaga agcaaagaaa 120
gcacaagctt ctggtgcaca aagtgcaaac gctagttatg gtactgaatt tgcaactgaa 180
acagatgtgc atgctgtgaa aaaacaaaat gcacaatcag ctgcaaaaca a 231

<210> SEQ ID NO 55
<211> LENGTH: 231
<212> TYPE: DNA
<213> ORGANISM: Unidentified Bacillus

<400> SEQUENCE: 55
aacaaggcaa cttctggcgc tagcattcaa agtacaaatg ctagttatgg tacagagttt 60
tcaactgaaa cagatgtgca agcagtaaaa caagcaaatg cacaatcaga agcaaagaaa 120
gcacaagctt ctggtgcaca aagtgcaaac gctagttatg gtactgaatt tgcaactgaa 180
acagatgtgc atgctgtgaa aaaacaaaat gcacaatcag ctgcaaaaca a 231

<210> SEQ ID NO 56
<211> LENGTH: 231
<212> TYPE: DNA
<213> ORGANISM: Bacillus thuringiensis

<400> SEQUENCE: 56
aacaaggcaa cttctggtgc tagcattcaa agtacaaatg ctagttatgg tacagagttt 60
tcaactgaaa cagatgtaca agcagtaaaa caagcaaacg cacaatcaga agcaaagaaa 120
gcacaagctt ctggtgcaca aagtgcaaac gctagttatg gtactgaatt tgcaactgaa 180
acagacgtgc atgctgtgaa aaaacaaaat gcacaatcag ctgcaaaaca a 231

<210> SEQ ID NO 57

<211> LENGTH: 231
<212> TYPE: DNA
<213> ORGANISM: Bacillus thuringiensis

<400> SEQUENCE: 57

| | |
|---|---|
| aacaaggcaa cttctggtgc tagcattcaa agtacaaatg ctagttatgg tacagagttt | 60 |
| tcaactgaaa cagatgtaca agcagtaaaa caagcaaacg cacaatcaga agcaaagaaa | 120 |
| gcacaagctt ctggtgcaca aagtgcaaac gctagttatg gtacagaatt tgcaactgaa | 180 |
| acagacgtgc atgctgtgaa aaaacaaaat gcacaatcag ctgcaaaaca a | 231 |

<210> SEQ ID NO 58
<211> LENGTH: 231
<212> TYPE: DNA
<213> ORGANISM: Bacillus thuringiensis

<400> SEQUENCE: 58

| | |
|---|---|
| aacaaggcaa cttctggtgc tagcattcaa agtacaaatg ctagttatgg tacagagttt | 60 |
| gcaactgaaa caaatgtaca agcagtaaaa caagcaaacg cacaatcaga agcaaagaaa | 120 |
| gcacaagctt ctggtgcaca aagtgcaaac gctagttatg gtacagaatt tgcaactgaa | 180 |
| acagacgtgc atgctgtgaa aaaacaaaat gctaagtcag ctgcaaaaca a | 231 |

<210> SEQ ID NO 59
<211> LENGTH: 231
<212> TYPE: DNA
<213> ORGANISM: Bacillus thuringiensis

<400> SEQUENCE: 59

| | |
|---|---|
| aacaaggcaa cttctggtgc tagcattcaa agtacaaatg ctagttatgg tacagagttt | 60 |
| gcaactgaaa caaatgtaca agcagtaaaa caagcaaacg cacaatcaga agcaaagaaa | 120 |
| gcacaagctt ctggtgcaca aagtgcaaac gctagttatg gtacagaatt tgcaactgaa | 180 |
| acagacgtgc atgctgtgaa aaaacaaaat gctaagtcag ctgcaaaaca a | 231 |

<210> SEQ ID NO 60
<211> LENGTH: 231
<212> TYPE: DNA
<213> ORGANISM: Bacillus thuringiensis

<400> SEQUENCE: 60

| | |
|---|---|
| aacaaggcaa cttctggtgc tagcattcaa agtacaaatg ctagttatgg tacagagttt | 60 |
| gcaactgaaa caaatgtaca agcagtaaaa caagcaaacg cacaatcaga agcaaagaaa | 120 |
| gcacaagctt ctggtgcaca aagtgcaaac gctagttatg gtacagaatt tgcaactgaa | 180 |
| acagacgtgc atgctgtgaa aaaacaaaat gctaagtcag ctgcaaaaca a | 231 |

<210> SEQ ID NO 61
<211> LENGTH: 231
<212> TYPE: DNA
<213> ORGANISM: Bacillus cereus

<400> SEQUENCE: 61

| | |
|---|---|
| aacaaagcaa cttctggtgc tagcattcaa agtacaaatg ctagttatgg tacagagttt | 60 |
| tcaactgaaa cagatgtaca agctgtaaaa caagcaaacg cacaatcaga agcaaaaaaa | 120 |
| gcacaagctt ctggtgcaca aagtgcaaac gctagttatg gtacagaatt tgcaactgaa | 180 |
| acagacgtgc attctgtgaa aaaacaaaat gctaagtcag ctgcaaaaca a | 231 |

<210> SEQ ID NO 62
<211> LENGTH: 231
<212> TYPE: DNA
<213> ORGANISM: Unidentified Bacillus

<400> SEQUENCE: 62
aacaaagcaa cttctggtgc tagcattcaa agtacaaatg ctagttatgg tacagagttt    60
tcaactgaaa cagatgtaca agctgtaaaa caagcaaacg cacaatcaga agcaaagaaa   120
gcacaagctt ctggtgcaca aagtgcaaac gctagttatg gtacagaatt tgcaactgaa   180
acagacgtgc attctgtgaa aaaacaaaat gctaagtcag ctgcaaaaca a            231

<210> SEQ ID NO 63
<211> LENGTH: 231
<212> TYPE: DNA
<213> ORGANISM: Bacillus cereus

<400> SEQUENCE: 63
aacaaagcaa cttctggtgc tagcattcaa agtacaaatg ctagttatgg tacagagttt 60
tcaactgaaa cagatgtaca agctgtaaaa caagcaaacg cacaatcaga agcaaagaaa 120
gcacaagctt ctggtgcaca aagtgcaaac gctagttatg gtacagaatt tgcaactgaa 180
acagacgtgc attctgtgaa aaaacaaaat gctaagtcag ctgcaaaaca a 231

<210> SEQ ID NO 64
<211> LENGTH: 231
<212> TYPE: DNA
<213> ORGANISM: Bacillus thuringiensis

<400> SEQUENCE: 64
aacaaagcaa cttctggtgc tagcattcaa agtacaaatg ctagttatgg tacagagttt 60
tcaactgaaa cagatgtaca agctgtaaaa caagcaaacg cacaatcaga agcaaagaaa 120
gcacaagctt ctggtgcaca aagtgcaaac gctagttatg gtacagaatt tgcaactgaa 180
acagacgtgc attctgtgaa aaaacaaaat gctaagtcag ctgcaaaaca a 231

<210> SEQ ID NO 65
<211> LENGTH: 231
<212> TYPE: DNA
<213> ORGANISM: Bacillus thuringiensis

<400> SEQUENCE: 65
aacaaagcaa cttctggtgc tagcattcaa agtacaaatg ctagttatgg tacagagttt 60
tcaactgaaa cagatgtaca agctgtaaaa caagcaaacg cacaatcaga agcaaagaaa 120
gcacaagctt ctggtgcaca aagtgcaaac gctagttatg gtacagaatt tgcaactgaa 180
acagacgtgc attctgtgaa aaaacaaaat gctaagtcag ctgcaaaaca a 231

<210> SEQ ID NO 66
<211> LENGTH: 231
<212> TYPE: DNA
<213> ORGANISM: Bacillus thuringiensis

<400> SEQUENCE: 66
aacaaagcaa cttctggtgc tagcattcaa agtacaaatg ctagttatgg tacagagttt 60
tcaactgaaa cagatgtaca agctgtaaaa caagcaaacg cacaatcaga agcaaagaaa 120
gcacaagctt ctggtgcaca aagtgcaaac gctagttatg gtacagaatt tgcaactgaa 180
acagacgtgc attctgtgaa aaaacaaaat gctaagtcag ctgcaaaaca a 231

-continued

<210> SEQ ID NO 67
<211> LENGTH: 231
<212> TYPE: DNA
<213> ORGANISM: Bacillus thuringiensis

<400> SEQUENCE: 67
aacaaagcaa cttctggtgc tagcattcaa agtacaaatg ctagttatgg tacagagttt 60
tcaactgaaa cagatgtaca agctgtaaaa caagcaaacg cacaatcaga agcaaagaaa 120
gcacaagctt ctggtgcaca aagtgcaaac gctagttatg gtacagaatt tgcaactgaa 180
acagacgtgc attctgtgaa aaaacaaaat gctaagtcag ctgcaaaaca a 231

<210> SEQ ID NO 68
<211> LENGTH: 231
<212> TYPE: DNA
<213> ORGANISM: Bacillus thuringiensis

<400> SEQUENCE: 68
aacaaagcaa cttctggtgc tagcattcaa agtacaaatg ctagttatgg tacagagttt 60
tcaactgaaa cagatgtaca agctgtaaaa caagcaaacg cacaatcaga agcaaagaaa 120
gcacaagctt ctggtgcaca aagtgcaaac gctagttatg gtacagaatt tgcaactgaa 180
acagacgtgc atgctgtgaa aaaacaaaat gctaagtcag ctgcaaaaca a 231

<210> SEQ ID NO 69
<211> LENGTH: 231
<212> TYPE: DNA
<213> ORGANISM: Bacillus thuringiensis

<400> SEQUENCE: 69
aacaaagcaa cttctggtgc tagcattcaa agtacaaatg ctagttatgg tacagagttt 60
tcaactgaaa cagatgtaca agctgtaaaa caagcaaacg cacaatcaga agcaaagaaa 120
gcacaagctt ctggtgcaca aagtgcaaac gctagttatg gtacagaatt tgcaactgaa 180
acagacgtgc attctgtgaa aaaacaaaat gctaagtcag ctgcaaaaca a 231

<210> SEQ ID NO 70
<211> LENGTH: 231
<212> TYPE: DNA
<213> ORGANISM: Bacillus thuringiensis

<400> SEQUENCE: 70
aacaaagcaa cttctggtgc tagcattcaa agtacaaatg ctagttatgg tacagagttt 60
tcaactgaaa cagatgtaca agctgtaaaa caagcaaacg cacaatcaga agcaaagaaa 120
gcacaagctt ctggtgcaca aagtgcaaac gctagttatg gtacagaatt tgcaactgaa 180
acagacgtgc attctgtgaa aaaacaaaat gctaagtcag ctgcaaaaca a 231

<210> SEQ ID NO 71
<211> LENGTH: 231
<212> TYPE: DNA
<213> ORGANISM: Bacillus thuringiensis

<400> SEQUENCE: 71
aacaaagcaa cttctggtgc tagcattcaa agtacaaatg ctagttatgg tacagagttt 60
tcaactgaaa cagatgtaca agctgtaaaa caagcaaacg cacaatcaga agcaaagaaa 120
gcacaagctt ctggtgcaca aagtgcaaac gctagttatg gtacagaatt tgcaactgaa 180
acagacgtgc attctgtgaa aaaacaaaat gctaagtcag ctgcaaaaca a 231

<210> SEQ ID NO 72
<211> LENGTH: 231
<212> TYPE: DNA
<213> ORGANISM: Bacillus thuringiensis

<400> SEQUENCE: 72
aacaaagcaa cttctggtgc tagcattcaa agtacaaatg ctagttatgg tacagagttt      60
tcaactgaaa cagatgtaca agctgtaaaa caagcaaacg cacaatcaga agcaaagaaa     120
gcacaagctt ctggtgcaca aagtgcaaac gctagttatg gtacagaatt tgcaactgaa     180
acagacgtgc attctgtgaa aaaacaaaat gctaagtcag ctgcaaaaca a              231

<210> SEQ ID NO 73
<211> LENGTH: 231
<212> TYPE: DNA
<213> ORGANISM: Bacillus thuringiensis

<400> SEQUENCE: 73
aacaaagcaa cttctggtgc tagcattcaa agtacaaatg ctagttatgg tacagagttt      60
tcaactgaaa cagatgtaca agctgtaaaa caagcaaacg cacaatcaga agcaaagaaa     120
gcacaagctt ctggtgcaca aagtgcaaac gctagttatg gtacagaatt tgcaactgaa     180
acagacgtgc attctgtgaa aaaacaaaat gctaagtcag ctgcaaaaca a              231

<210> SEQ ID NO 74
<211> LENGTH: 231
<212> TYPE: DNA
<213> ORGANISM: Bacillus cereus

<400> SEQUENCE: 74
aacaaggcaa cttctggtgc tagcattcaa agtacaaatg ctagttatgg tacagagttt      60
tcaactgaaa cagatgtaca agctgtaaaa caagcaaacg cacaatcaga agcaaagaaa     120
gcacaagctt ctggtgcaca aagtgcaaac gctagttatg gtacagaatt tgcaactgaa     180
acagacgtgc attctgtgaa aaaacaaaat gctaagtcag ctgcaaaaca a              231

<210> SEQ ID NO 75
<211> LENGTH: 231
<212> TYPE: DNA
<213> ORGANISM: Bacillus thuringiensis

<400> SEQUENCE: 75
aacaaggcaa cttctggtgc tagcattcaa agtacaaatg ctagttatgg tacagagttt      60
gcgactgaaa caaatgtaca agcagtaaaa caagcaaacg cacaatcaga agcaaagaaa     120
gcacaagctt ctggtgcaca aagtgcaaac gctagttatg gtacagaatt tgcaactgaa     180
acagacgtgc atgctgtgaa aaaacaaaat gctaagtcag ctgcaaaaca a              231

<210> SEQ ID NO 76
<211> LENGTH: 231
<212> TYPE: DNA
<213> ORGANISM: Bacillus thuringiensis

<400> SEQUENCE: 76
aacaaggcaa cttctggtgc tagcattcaa agtacaaatg ctagttatgg tacagagttt      60
gcgactgaaa caaatgtaca agcagtaaaa caagcaaacg cacaatcaga agcaaagaaa     120
gcacaagctt ctggtgcaca aagtgcaaac gctagttatg gtacagaatt tgcaactgaa     180

```
acagacgtgc atgctgtgaa aaacaaaat gctaagtcag ctgcaaaaca a          231
```

<210> SEQ ID NO 77
<211> LENGTH: 231
<212> TYPE: DNA
<213> ORGANISM: Bacillus thuringiensis

<400> SEQUENCE: 77

```
aacaaggcaa cttctggtgc tagcattcaa agtacaaatg ctagttatgg tacagagttt   60
gcgactgaaa caaatgtaca agcagtaaaa caagcaaacg cacaatcaga agcaaagaaa  120
gcacaagctt ctggtgcaca aagtgcaaac gctagttatg gtacagaatt tgcaactgaa  180
acagacgtgc atgctgtgaa aaacaaaat gctaagtcag ctgcaaaaca a            231
```

<210> SEQ ID NO 78
<211> LENGTH: 231
<212> TYPE: DNA
<213> ORGANISM: Bacillus thuringiensis

<400> SEQUENCE: 78

```
aacaaggcaa cttctggtgc tagcattcaa agtacaaatg ctagttatgg tacagagttt   60
gcgactgaaa caaatgtaca agcagtaaaa caagcaaacg cacaatcaga agcaaagaaa  120
gcacaagctt ctggtgcaca aagtgcaaac gctagttatg gtacagaatt tgcaactgaa  180
acagacgtgc atgctgtgaa aaacaaaat gctaagtcag ctgcaaaaca a            231
```

<210> SEQ ID NO 79
<211> LENGTH: 231
<212> TYPE: DNA
<213> ORGANISM: Bacillus thuringiensis

<400> SEQUENCE: 79

```
aacaaggcaa cttctggtgc tagcattcaa agtacaaatg ctagttatgg tacagagttt   60
gcgactgaaa caaatgtaca agcagtaaaa caagcaaacg cacaatcaga agcaaagaaa  120
gcacaagctt ctggtgcaca aagtgcaaac gctagttatg gtacagaatt tgcaactgaa  180
acagacgtgc atgctgtgaa aaacaaaat gctaagtcag ctgcaaaaca a            231
```

<210> SEQ ID NO 80
<211> LENGTH: 231
<212> TYPE: DNA
<213> ORGANISM: Bacillus thuringiensis

<400> SEQUENCE: 80

```
aacaaggcaa cttctggtgc tagcattcaa agtacaaatg ctagttatgg tacagagttt   60
gcgactgaaa caaatgtaca agcagtaaaa caagcaaacg cacaatcaga agcaaagaaa  120
gcacaagctt ctggtgcaca aagtgcaaac gctagttatg gtacagaatt tgcaactgaa  180
acagacgtgc atgctgtgaa aaacaaaat gctaagtcag ctgcaaaaca a            231
```

<210> SEQ ID NO 81
<211> LENGTH: 231
<212> TYPE: DNA
<213> ORGANISM: Bacillus thuringiensis

<400> SEQUENCE: 81

```
aacaaggcaa cttctggtgc tagcattcaa agtacaaatg ctagttatgg tacagaattt   60
gctactgaaa caaatgtaca agcagtaaaa caagcaaacg cacaatcaga agcaaagaaa  120
gcacaagctt ctggtgcaca aagtgcaaac gctagttatg gtacagaatt tgcaactgaa  180
```
acagacgtgc atgctgtgaa aaacaaaat gctaagtcag ctgcaaaaca a            231

<210> SEQ ID NO 82
<211> LENGTH: 231
<212> TYPE: DNA
<213> ORGANISM: Bacillus thuringiensis

<400> SEQUENCE: 82
aacaaggcaa cttctggtgc tagcattcaa agtacaaatg ctagttatgg tacagaattt    60
gctactgaaa caaatgtaca agcagtaaaa caagcaaacg cacaatcaga agcaaagaaa   120
gcacaagctt ctggtgcaca aagtgcaaac gctagttatg gtacagaatt tgcaactgaa   180
acagacgtgc atgctgtgaa aaacaaaat gctaagtcag ctgcaaaaca a            231

<210> SEQ ID NO 83
<211> LENGTH: 231
<212> TYPE: DNA
<213> ORGANISM: Bacillus cereus

<400> SEQUENCE: 83
aacaaggcaa cttctggtgc tagcattcaa agtacaaatg ctagttatgg tacagaattt    60
gctactgaaa caaatgtaca agcagtaaaa caagcaaacg cacaatcaga agcaaagaaa   120
gcacaagctt ctggtgcaca aagtgcaaac gctagttatg gtacagaatt tgcaactgaa   180
acagacgtgc atgctgtgaa aaacaaaat gctaagtcag ctgcaaaaca a            231

<210> SEQ ID NO 84
<211> LENGTH: 231
<212> TYPE: DNA
<213> ORGANISM: Bacillus thuringiensis

<400> SEQUENCE: 84
aacaaggcaa cttctggtgc tagcattcaa agtacaaatg ctagttatgg tacagagttt    60
gcgactgaaa caaatgtaca agcagtaaaa caagcaaacg cacaatcaga agcaaagaaa   120
gcacaagctt ctggtgcaca aagtgcaaac gctagttatg gtacagaatt tgcaactgaa   180
acagacgtgc atgctgtgaa aaacaaaat gctaagtcag ctgcaaaaca a            231

<210> SEQ ID NO 85
<211> LENGTH: 231
<212> TYPE: DNA
<213> ORGANISM: Bacillus thuringiensis

<400> SEQUENCE: 85
aacaaggcaa cttctggtgc tagcattcaa agtacaaatg ctagttatgg tacagagttt    60
gcgactgaaa caaatgtaca agcagtaaaa caagcaaacg cacaatcaga agcaaagaaa   120
gcacaagctt ctggtgcaca aagtgcaaac gctagttatg gtacagaatt tgcaactgaa   180
acagacgtgc atgctgtgaa aaacaaaat gctaagtcag ctgcaaaaca a            231

<210> SEQ ID NO 86
<211> LENGTH: 231
<212> TYPE: DNA
<213> ORGANISM: Bacillus anthracis

<400> SEQUENCE: 86
aacaaggcaa cttctggtgc tagcattcaa agtacaaatg ctagttatgg tacagagttt    60
gcgactgaaa caaatgtaca agcagtaaaa caagcaaacg cacaatcaga agcaaagaaa   120

```
gcacaagctt ctggtgcaca aagtgcaaac gctagctatg gtacagaatt tgcaactgaa    180
acagacgtgc atgctgtgaa aaaacaaaat gctaagtcag ctgcaaaaca a              231
```

<210> SEQ ID NO 87
<211> LENGTH: 237
<212> TYPE: DNA
<213> ORGANISM: Bacillus anthracis

<400> SEQUENCE: 87

```
aacaaggcaa cttctggtgc tagcattcaa agcacaaatg ctagttatgg tacagagttt     60
gcgactgaaa caaatgtaca agcagtaaaa caagcaaacg cacaatcaga agctaagaaa    120
gcgcaagctt ctggtgctag cattcaaagc acaaatgcta gttatggtac agaatttgca    180
actgaaacag acgtgcatgc tgtgaaaaaa caaaatgcac aatcagctgc aaaacaa       237
```

<210> SEQ ID NO 88
<211> LENGTH: 77
<212> TYPE: PRT
<213> ORGANISM: Bacillus thuringiensis

<400> SEQUENCE: 88

Asn Lys Ala Thr Ser Gly Ala Ser Ile Gln Ser Thr Asn Ala Ser Tyr
 1               5                  10                  15

Gly Thr Glu Phe Ser Thr Glu Thr Asp Val Gln Ala Val Lys Gln Ala
            20                  25                  30

Asn Ala Gln Ser Glu Ala Lys Lys Ala Gln Ala Ser Gly Ala Gln Ser
        35                  40                  45

Ala Asn Ala Ser Tyr Gly Thr Glu Phe Ala Thr Glu Thr Asp Val His
    50                  55                  60

Ser Val Lys Lys Gln Asn Ala Lys Ser Ala Ala Lys Gln
65                  70                  75

<210> SEQ ID NO 89
<211> LENGTH: 77
<212> TYPE: PRT
<213> ORGANISM: Bacillus cereus

<400> SEQUENCE: 89

Asn Lys Ala Thr Ser Gly Ala Ser Ile Gln Ser Thr Asn Ala Ser Tyr
 1               5                  10                  15

Gly Thr Glu Phe Ser Thr Glu Thr Asp Val Gln Ala Val Lys Gln Ala
            20                  25                  30

Asn Ala Gln Ser Glu Ala Lys Lys Ala Gln Ala Ser Gly Ala Gln Ser
        35                  40                  45

Ala Asn Ala Ser Tyr Gly Thr Glu Phe Ala Thr Glu Thr Asp Val His
    50                  55                  60

Ser Val Lys Lys Gln Asn Ala Lys Ser Ala Ala Lys Gln
65                  70                  75

<210> SEQ ID NO 90
<211> LENGTH: 77
<212> TYPE: PRT
<213> ORGANISM: Bacillus thuringiensis

<400> SEQUENCE: 90

Asn Lys Ala Thr Ser Gly Ala Ser Ile Gln Ser Thr Asn Ala Ser Tyr
 1               5                  10                  15

Gly Thr Glu Phe Ala Thr Glu Thr Asn Val Gln Ala Val Lys Gln Ala
            20                  25                  30

Asn Ala Gln Ser Glu Ala Lys Lys Ala Gln Ala Ser Gly Ala Gln Ser
                35                  40                  45

Ala Asn Ala Ser Tyr Gly Thr Glu Phe Ala Thr Glu Thr Asp Val His
    50                  55                  60

Ala Val Lys Lys Gln Asn Ala Lys Ser Ala Ala Lys Gln
65                  70                  75

<210> SEQ ID NO 91
<211> LENGTH: 77
<212> TYPE: PRT
<213> ORGANISM: Bacillus thuringiensis

<400> SEQUENCE: 91

Asn Lys Ala Thr Ser Gly Ala Ser Ile Gln Ser Thr Asn Ala Ser Tyr
1               5                   10                  15

Gly Thr Glu Phe Ser Thr Glu Thr Asp Val Gln Ala Val Lys Gln Ala
            20                  25                  30

Asn Ala Gln Ser Glu Ala Lys Lys Ala Gln Ala Ser Gly Ala Gln Ser
                35                  40                  45

Ala Asn Ala Ser Tyr Gly Thr Glu Phe Ala Thr Glu Thr Asp Val His
    50                  55                  60

Ala Val Lys Lys Gln Asn Ala Gln Ser Ala Ala Lys Gln
65                  70                  75

<210> SEQ ID NO 92
<211> LENGTH: 79
<212> TYPE: PRT
<213> ORGANISM: Bacillus anthracis

<400> SEQUENCE: 92

Asn Lys Ala Thr Ser Gly Ala Ser Ile Gln Ser Thr Asn Ala Ser Tyr
1               5                   10                  15

Gly Thr Glu Phe Ala Thr Glu Thr Asn Val Gln Ala Val Lys Gln Ala
            20                  25                  30

Asn Ala Gln Ser Glu Ala Lys Lys Ala Gln Ala Ser Gly Ala Ser Ile
                35                  40                  45

Gln Ser Thr Asn Ala Ser Tyr Gly Thr Glu Phe Ala Thr Glu Thr Asp
    50                  55                  60

Val His Ala Val Lys Lys Gln Asn Ala Gln Ser Ala Ala Lys Gln
65                  70                  75

<210> SEQ ID NO 93
<211> LENGTH: 76
<212> TYPE: PRT
<213> ORGANISM: Bacillus mycoides

<400> SEQUENCE: 93

Asn Lys Ala Thr Ser Gly Ala Ser Ile Gln Ser Thr Asn Ala Ser Tyr
1               5                   10                  15

Gly Thr Glu Phe Ala Thr Glu Thr Asn Val Gln Ala Val Lys Gln Ala
            20                  25                  30

Asn Ala Gln Ser Glu Ala Gln Lys Ala Gln Ala Ser Ala Ala Gln Ser
                35                  40                  45

Ala Asn Ala Ser Tyr Gly Thr Glu Phe Ala Thr Glu Thr Asp Val His
    50                  55                  60

Ala Val Lys Lys Gln Asn Ala Gln Ser Ala Ala Lys
65                  70                  75

<210> SEQ ID NO 94
<211> LENGTH: 20
<212> TYPE: DNA
<213> ORGANISM: Bacillus anthracis

<400> SEQUENCE: 94
gttatggtac agagtttgcg                                              20

<210> SEQ ID NO 95
<211> LENGTH: 19
<212> TYPE: DNA
<213> ORGANISM: Bacillus anthracis

<400> SEQUENCE: 95
ttgttttgca gctgattgt                                               19

<210> SEQ ID NO 96
<211> LENGTH: 232
<212> TYPE: DNA
<213> ORGANISM: Bacillus cereus

<400> SEQUENCE: 96
aacaaagcaa cttctggtgc tagcattcaa agtacaaatg ctagttatgg tacagagttt     60
tcaactgaaa cagatgtaca agctgtaaaa caagcaaacg cacaatcaga agcaaagaaa    120
gcacaagctt ctggtgcaca aagtgcaaac gctagttatg gtacagaatt tgcaactgaa    180
acagacgtgc attctgtgaa aaacaaaat gctaagtcag ctgcaaaaca aa            232

<210> SEQ ID NO 97
<211> LENGTH: 238
<212> TYPE: DNA
<213> ORGANISM: Bacillus anthracis

<400> SEQUENCE: 97
aacaaggcaa cttctggtgc tagcattcaa agcacaaatg ctagttatgg tacagagttt     60
gcgactgaaa caaatgtaca agcagtaaaa caagcaaacg cacaatcaga agctaagaaa    120
gcgcaagctt ctggtgctag cattcaaagc acaaatgcta gttatggtac agaatttgca    180
actgaaacag acgtgcatgc tgtgaaaaaa caaaatgcac aatcagctgc aaaacaaa     238

<210> SEQ ID NO 98
<211> LENGTH: 231
<212> TYPE: DNA
<213> ORGANISM: Bacillus cereus

<400> SEQUENCE: 98
aacaaagcaa cttctggtgc tagcattcaa agtacaaatg ctagttatgg tacagagttt     60
tcaactgaaa cagatgtaca agctgtaaaa caagcaaacg cacaatcaga agcaaagaaa    120
gcacaagctt ctggtgcaca aagtgcaaac gctagttatg gtacagaatt tgcaactgaa    180
acagacgtgc attctgtgaa aaacaaaat gctaagtcag ctgcaaaaca a             231

<210> SEQ ID NO 99
<211> LENGTH: 237
<212> TYPE: DNA
<213> ORGANISM: Bacillus anthracis

<400> SEQUENCE: 99
aacaaggcaa cttctggtgc tagcattcaa agcacaaatg ctagttatgg tacagagttt     60
gcgactgaaa caaatgtaca agcagtaaaa caagcaaacg cacaatcaga agctaagaaa    120

```
gcgcaagctt ctggtgctag cattcaaagc acaaatgcta gttatggtac agaatttgca      180
actgaaacag acgtgcatgc tgtgaaaaaa caaaatgcac aatcagctgc aaaacaa         237
```

<210> SEQ ID NO 100
<211> LENGTH: 21
<212> TYPE: DNA
<213> ORGANISM: Artificial Sequence
<220> FEATURE:
<223> OTHER INFORMATION: Description of Artificial Sequence:
      Oligonucleotides  evaluated for use as B.
      anthracis probes

<400> SEQUENCE: 100

```
gcatttgtgc tttgaatgct a                                                21
```

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence:
      Oligonucleotides  evaluated for use as B.
      anthracis probes

<400> SEQUENCE: 101

```
catttgtgct ttgaatgcta                                                  20
```

<210> SEQ ID NO 102
<211> LENGTH: 19
<212> TYPE: DNA
<213> ORGANISM: Artificial Sequence
<220> FEATURE:
<223> OTHER INFORMATION: Description of Artificial Sequence:
      Oligonucleotides  evaluated for use as B.
      anthracis probes

<400> SEQUENCE: 102

```
agcttctggt gctagcatt                                                   19
```

<210> SEQ ID NO 103
<211> LENGTH: 22
<212> TYPE: DNA
<213> ORGANISM: Bacillus globigii

<400> SEQUENCE: 103

```
acatggctaa ctcaaacaac aa                                               22
```

<210> SEQ ID NO 104
<211> LENGTH: 25
<212> TYPE: DNA
<213> ORGANISM: Bacillus globigii

<400> SEQUENCE: 104

```
ggttttgttt tcttacttgt tgtac                                            25
```

<210> SEQ ID NO 105
<211> LENGTH: 26
<212> TYPE: DNA
<213> ORGANISM: Clostridium perfringens

<400> SEQUENCE: 105

```
aataactaag gaggaatgaa aaatgt                                           26
```

<210> SEQ ID NO 106

-continued

<211> LENGTH: 25
<212> TYPE: DNA
<213> ORGANISM: Bacillus anthracis

<400> SEQUENCE: 106
ttgttctacc attcttttaa ccatt 25

<210> SEQ ID NO 107
<211> LENGTH: 7
<212> TYPE: DNA
<213> ORGANISM: Artificial Sequence
<220> FEATURE:
<223> OTHER INFORMATION: Description of Artificial Sequence: Bacillus anthracis probe sequence

<400> SEQUENCE: 107 tagcatt 7

<210> SEQ ID NO 108
<211> LENGTH: 7
<212> TYPE: DNA
<213> ORGANISM: Artificial Sequence
<220> FEATURE:
<223> OTHER INFORMATION: Description of Artificial Sequence: Bacillus anthracis probe sequence

<400> SEQUENCE: 108 aatgcta 7

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Bacillus anthracis probe sequence

<400> SEQUENCE: 109
tagcattcaa agcacaaatg 20

<210> SEQ ID NO 110
<211> LENGTH: 361
<212> TYPE: DNA
<213> ORGANISM: Bacillus globigii

<400> SEQUENCE: 110
attctaattg tcgtggaggt gataaacatg gctaactcaa acaacttcag caaaacaaac 60
gctcaacaag taagaaaaca aaaccaacaa tcagcttctg gccaaggtca gtttggtaca 120
gaatttgcta gcgaaacaaa cgtacaacaa gtaagaaaac aaaaccagca atcagctgct 180
ggacaaggtc aattcggcac tgaattcgct agtgaaactg atgctcagca agtaagacag 240
caaaaccaat ctgctgaaca aaacaaacaa caaaacagct aatcactgaa acagaaaaaa 300
agcacttcat cctcgggtgg aagtgctttt ttctttttat aaaacgacaa aacttgtgga 360
a 361

<210> SEQ ID NO 111
<211> LENGTH: 384
<212> TYPE: DNA
<213> ORGANISM: Bacillus subtilis

SEQUENCE: 111 ttgacgcgga cgctcactgc tcgtttaaaa atttttaaaa aagaggaata gctatacgat 60

-continued

| | | | | | |
|---|---|---|---|---|---|
| cacctgcaca | ttctaatgac | cgtggaggtg | ataacaatgg | ctaactcaaa | taacttcagc | 120
| aaaacaaacg | ctcaacaagt | tagaaaacaa | aaccaacaat | cagctgctgg | tcaaggtcaa | 180
| tttggcactg | aatttgctag | cgaaacaaac | gctcagcaag | tcagaaaaca | aaaccagcaa | 240
| tcagctggac | aacaaggtca | attcggcact | gaattcgcta | gtgaaactga | cgcacagcag | 300
| gtaagacagc | aaaaccaatc | tgctgaacaa | aacaaacaac | aaaacagcta | atcactgaaa | 360
| cagaaaaaag | cacttcatct | tcgg | | | | 384

<210> SEQ ID NO 112
<211> LENGTH: 6
<212> TYPE: DNA
<213> ORGANISM: Bacillus anthracis

<400> SEQUENCE: 112 agcatt                                                                6

US 6,472,155 B1

SPECIES SPECIFIC IDENTIFICATION OF SPORE-PRODUCING MICROBES USING THE GENE SEQUENCE OF SMALL ACID-SOLUBLE SPORE COAT PROTEINS FOR AMPLIFICATION BASED DIAGNOSTICS

REFERENCE TO RELATED APPLICATIONS

This application claims priority benefit of U.S. provisional application No. 60/138,167, filed on Jun. 8, 1999, and U.S. provisional application No. 60/192,206, filed on Mar. 27, 2000, which are incorporated herein by reference.

STATEMENT OF GOVERNMENT SUPPORT

This invention was made under work supported by the U.S. Department of Energy under DOE Contract No.: DE-AC03-76SF00098. The government has certain rights in this invention.

FIELD OF THE INVENTION

The present invention relates to methods and compositions for the detection of Bacillus species such as *Bacillus anthracis* and *Bacillus globigii* as well as *Clostridium perfringens*. It relies on nucleic acid sequence differences in spore protein genes carried in the genomic sequence of these organisms.

BACKGROUND OF THE INVENTION

The genus Bacillus is composed of rod-shaped, gram-positive, aerobic or (under some conditions) anaerobic bacteria widely found in soil and water. Most strains of Bacillus are not pathogenic for humans and only infect them incidentally in their role as soil organisms; a notable exception is *Bacillus anthracis*, which causes anthrax in humans and domestic animals.

In addition to its role as a naturally occurring pathogen, *Bacillus anthracis* may also be used as a biological weapon. Because Bacillus organisms are widely distributed in the environment, and because they are very closely related genetically, there is need for a reliable method to distinguish species members in various types of samples.

Considerable efforts have been made to develop sensitive, species specific tests for Bacillus microorganisms with only limited results. Most of the *Bacillus anthracis* PCR detection systems have targeted plasmid sequences, yet mobility of these genetic elements make them an unreliable detection target. Several of the PCR type assays to genomic sequences target non-gene-coding sequences, which often proves not to correlate well with species identity. The weaknesses in each of these systems underscores the need for a more reliable Bacillus identification method.

SUMMARY OF THE INVENTION

The subject invention provides novel methods and materials for specifically identifying certain rod-shaped, gram-positive bacteria. These methods and materials rely on the discovery that certain small acid-soluble protein (sasp) gene targets are present in the bacterial coats of Bacillus and Clostridium organisms. These sasp gene targets may be identified by a technique described here as "heterologous PCR". More specifically, these methods and materials provide means for specifically identifying certain members of the Bacillus genus, especially *Bacillus anthracis* and *Bacillus globigii*, and members of the Clostridium genus, especially *Clostridium perfringens*. Using heterologous PCR, novel gene targets are identified that yield species-specific regions for detection and identification. Based on this technique, assay techniques for identifying the organisms *Bacillus anthracis*, *Bacillus globigii* and *Clostridium perfringens* have been developed.

Another aspect of the invention comprises use of a small acid soluble protein (sasp-B) gene sequence in *Bacillus anthracis* that contains a specific region of stable nucleotide insertion absent in even the closest Bacillus relatives. This unique biomarker is a probe-binding region for the specific detection of *Bacillus anthracis*. Additional regions of sequence within the gene were used to develop a *Bacillus anthracis* specific amplification and detection system. The system is capable of distinguishing *Bacillus anthracis* from near neighbors during two phases of the amplified assay: during the amplification reaction, and by probe hybridization to the *Bacillus anthracis* specific biomarker within the amplified product for sequence confirmation.

As another aspect of the invention, the present *Bacillus anthracis* detection system either alone, or multiplexed with one or more additional genomic and/or virulence plasmid markers, is of use as a diagnostic or confirmatory tool in Public Health and clinical laboratories, as well as in the law enforcement sector. The system may be adapted to a variety of amplification and detection platforms in order to accommodate the technical and fiscal capabilities of the laboratory, or used in 'field' settings.

As yet another aspect of the invention, building upon the discovery that small acid-soluble spore protein genes maintain species-specific sequence signatures, analogous regions were identified among the sasp of *Bacillus globigii* (which is used as a non-pathogenic 'surrogate' for *Bacillus anthracis* in research and development applications, defense, and emergency response modeling, etc.). Taking advantage of this discovery, *Bacillus globigii* specific PCR was designed and reduced to practice.

Another aspect of the invention is to provide a two-step amplification/detection system. A particular sasp gene is selected for amplification, and its identity determined by a species-specific probe. Although the present invention is described in detail in connection with a PCR, it is understood that, based on the present teachings, other amplification and/or identification systems could be devised.

BRIEF DESCRIPTION OF THE DRAWINGS

FIG. 1. is a multiple ClustalW DNA Sequence Alignment of sasp-B Amplicons from 38 *Bacillus anthracis* strains (Seq. ID No. 13 through 50). Bases 1–90 are in FIG. 1A, 91–180 are in FIG. 1-B, and 181–240 are in 1C.

FIG. 2. is a ClustalW multiple sasp-B DNA Sequence Alignment of *Bacillus anthracis*, *Bacillus thuringiensis* and *Bacillus cereus* strains (Seq. ID No. 51 through 87). Bases 1–90 are in FIG. 2A, 91–180 are in FIG. 2-B, and 181–240 are in 2C.

FIG. 3. is a representation of *Bacillus globigii* specific PCR primers targeting Bg sasp-gamma

DETAILED DESCRIPTION OF THE PREFERRED EMBODIMENT

Described herein are regions of genomic sequence with patterns unique to the target organisms (*Bacillus anthracis*, *Bacillus globigii* and *Clostridium perfringens*) from which primers and probes were designed for specific amplification of target organism DNA, and where feasible, confirmation of amplicon sequence by probe hybridization. Spore coat and spore structural genes were studied because their products are intimately linked with the organism's environmental niche and phenotype, and therefore distinctly identify each species. In the case of *Bacillus anthracis*, very little genomic sequence data is available, hence published sequence listings from closely related species were used as a starting point from which primers for amplification of *Bacillus anthracis* DNA (a process commonly known as 'heterologous PCR') were designed. Heterologous PCR, then, means PCR using primers known to hybridize to one target to amplify, under conditions of low stringency, another target, in this case, from another species of unknown sequence in the target gene. Some 27 spore genes were screened via heterologous PCR and scores of reaction products sequenced before a sufficiently definitive region of sequence was identified for anthracis specific primer and probe design. The signature which satisfied the specificity criteria, and which is the key to this invention, was found within the coding sequence of the sasp spore structural protein.

EXAMPLE 1

Database Search & Primer Design Example
(*Bacillus anthracis* Primer/Probe Design)

Public databases GenBank and European Molecular Biology Laboratory (EMBL) were queried for "small acid-soluble spore protein" (sasp) DNA sequences. Three *Bacillus cereus* small acid-soluble protein genes were selected from GenBank for consideration (*Bacillus cereus* being one of the closest relatives to *Bacillus anthracis*). GenBank accession numbers for these sasp-B DNA sequences are: M13059 for *Bacillus cereus* sasp-1, M13060 for *Bacillus cereus* sasp-2, and M16813 for *Bacillus cereus* sasp-B.

Primer sequences were located within each sasp sequence which would maximize the likelihood of amplifying non-homologous sequences. For instance, whenever possible the 3' end of a primer was concluded with one or more thymidine residues. Potential primer sequences were analyzed using Oligo 4.0 primer design software (National Biosciences, Plymouth, Minn.) for potential hairpin or concatomers, which might interfere with hybridization to target DNA. Also using Oligo 4.0 primer design software (National Biosciences, Plymouth, Minn.), primer sequences were adjusted to match their melting temperatures as closely as possible to one another, which generally enhances reaction specificity. The sequence similarity search tool BLAST was queried with the primer sequences in order to insure that the primers did not recognize any bacterial (or other microbial) sequences except the targeted Bacillus species. Primers were synthesized (Sequence IDs No.1 through 6) using the PerSeptive Biosystems Expedite nucleic acid synthesis system (Perkin Elmer, Norwalk, Conn.). Oligos were released from columns by incubation in 29.3% ammonium hydroxide at 55° C. overnight, followed by evaporation of ammonium hydroxide using the SpeedVac 1SS110 (Savant Corp.). Primers were resuspended in 10 millimolar tris buffer, pH 8.3, and their concentration measured with a spectrophotometer.

Shown below are primers designed from *Bacillus cereus* sequences for heterologous PCR and sequencing of *Bacillus anthracis*, as described in Example 2.

Primer name

Bcsasp-B 5' ATGAGTAAAAAACAACAAGGTTAT (SEQ ID NO: 1)

Bcsasp-B 3' CTGATTTGAGCTAGAAGATTGTGA (SEQ ID NO: 2)

Bcsasp-1 5' ATGGGAAAAAATAATAGTGGAAGT (SEQ ID NO: 3)

Bcsasp-1 3' GCGGTTAGCTCTACCACCAAGT (SEQ ID NO: 4)

Bcsasp-2 5' ATGTCAGCTAGCACAAATAAATT (SEQ ID NO: 5)

Bcsasp-2 3' TTATTTTTGGTAACCGCCTAA (SEQ ID NO: 6)

The primers are named according to their corresponding *Bacillus cereus* sasp.

EXAMPLE 2

Amplification of Bacillus Species Using Sasp Primers, and Analysis of Reaction Products DNA was prepared according to the method described by Zhou (Zhou, J., Bruns, M., and Jiedje, J. 1996. "DNA recovery from soils of diverse composition." Appl. Environ. Microbiol. 62:316–322, 1996) from a non-infectious vegetative cells of *Bacillus anthracis* and *Bacillus cereus* type 168 (Bacillus Genetic Stock Center). The concentration of the purified DNA was determined by measuring the optical density at 260 nanometer wavelength using the Du 640 spectrophotometer (Beckman, Palo Alto), and by visual comparison to DNA standards of known quantity via agarose gel electrophoresis (Sambrook et. al. Molecular Cloning, 1989, Cold Spring Harbor Laboratory Press).

For initial trial of the new primers, Tris buffer at pH 8.3, 8.8, and 9.2 was evaluated along with potassium chloride at (final) concentrations of 25 mM and 75 mM and magnesium chloride at (final) concentrations of 1.5 and 3.5 mM were screened using OptiPrime 10×buffers (Stratagene, La Jolla, Calif.), in order to determine favorable reaction conditions for the new primers. Reaction volumes were 100 microliters and contained approximately 100 nanograms of target DNA (and in the case of negative controls, no DNA).

A GeneAmp 9600 PCR System (Perkin Elmer, Norwalk, Conn.) was programmed as follows for thermalcycling of the reaction: A 5 minute 94 degree C. initial denaturation step was followed by 40 three step cycles of 94 degrees C. for 30 sec., 50 degrees C. for 30 sec., 72 degrees C. for 30 sec. A final extension step of 7 minutes at 72 degrees C. completed the thermalcycling.

Amplification products were viewed by ethidium bromide stained nusieve/agarose slab gel electrophoresis. Ten microliters of PCR product was mixed with 2 microliters of 6×gel loading dye (a filter sterilized solution of 0.25% bromophenol blue plus 40% (wt/vol) sucrose in double distilled sterile water). A molecular weight marker ladder of 100 base pair DNA fragments (Life Technologies, Gaithersburg, Md.) was run alongside the amplicons in order to gauge the size of the PCR products. The expected size of reaction products based on the primer locations within the *B. cereus* DNA sequence are: 213 base pairs for sasp-1, 198 base pairs for sasp-2, and 279 base pairs for sasp-B.

Results of this initial experiment: The major products (as judged by band intensity when viewed by gel) from amplification of *Bacillus anthracis* DNA were the same size as the major products of *Bacillus cereus* amplification using each of the three primers, regardless of the reaction mixture employed. Thus, it appeared that a *Bacillus anthracis* sasp gene sequence had been obtained.

EXAMPLE 3

DNA Sequence Analysis of *Bacillus cereus* sasp-B Primed PCR Products from *Bacillus anthracis*

*Bacillus anthracis* PCR product from Example 2 was separated from primers and other reactants using the QIAquick Gel Extraction kit (Qiagen, Valencia, Calif.), and sequenced using the Dye Terminator Cycle Sequencing Kit (PE Biosystems, Foster City, Calif.) using the same *Bacillus cereus* sasp-B primers used to generate the product being sequenced. Sequencing reactions were performed in a TC-9600 thermalcycler (Perkin Elmer, Norwalk, Conn.). The completed sequencing reaction was electrophoresed and the sequence recorded on a Applied Biosystems Prism 377 Automated Sequencer (PE Biosystems, Foster City, Calif.). Since the PCR products were less than 300 bases, the entire length of each product was sequenced in a single run. The small size also made it possible to check the sequence by alignment of the two strands to one another. After inverting one strand with Gene Jockey sequence conversion software (BioSoft, Cambridge, UK), the strands were aligned using the Baylor College of Medicine ClustalW online multiple sequence alignment utility. CLUSTAL W is described in Thompson, J. D. Higgins, D. G. Gibson, T. J. (1994) Clustal W: improving the sensitivity of progressive multiple sequence alignment through sequence weighting, position specific gap penalties and weight matrix choice. Nucl. Acids Res. 22:4673–4680. Where there was discrepancy between the two strands (i.e. where the bases did not match in the alignment), electrophoretograms of the sequencing gel run were examined (using the PE Biosystems Editview utility) in order to resolve the discrepancy.

Finished *Bacillus anthracis* sequence was aligned with *Bacillus cereus* published sequence and the differences analyzed. Of greatest interest was the six base region in the *Bacillus anthracis* sasp-B amplicon which was not present in the *Bacillus cereus* published sequence. Alignments of the *Bacillus anthracis* sequence with the published *Bacillus cereus* sequence for the region between each primer pair follow:

In these alignments, dots signify a match with the sequence shown; only mismatches are spelled out, in order to emphasize them. Primer sequences are not included, but would be extensions of the 5' and 3' ends of the sequences shown.

The *Bacillus anthracis* and *B. cereus* sasp-1
Sequence Alignment did not Show Significant
Differences B.cer   1   CGTAATGAAGTATTAGTTCGAGGCGCT-
GAACAAGCTCTTGATCAAATGAAATATGAAATT
B.anth  1   .........T.............T.......
B.cer  61   GCACAAGAGTTTGGTGTACAACTTGGTG-
CAGATACAACAGCTCGTTCAAACGGATCTGTT
B.anth 61   ................................T........
B.cer 121   GGTGGTGAAATTACAAAACGTTTAGTAG-
CAATGGCAGAACA (SEQ ID NO: 7)
B.anth 121  ...............................T..... (SEQ ID NO: 8)

The *Bacillus anthracis* and *B. cereus* Sasp-2
Sequence Alignment did not Show Significant
Differences B.cer   1   AGCGGTTCCTGGTGCTGAATCAGCATTA-
GACCAAATGAAATACGAAATCGCTCAAGAGTT
B.anth  1   ......................................
B.cer  61   TGGTGTTCAACTTGGAGCTGATGCAA-
CAGCTCGCGCTAACGGTTCTGTTGGTGGCGAAAT
B.anth 61   ..........................................
B.cer 121   CACTAAACGTCTAGTTTCACTAGCTGAG-
CAACAA (SEQ ID NO: 9)
B.anth 121  ................................ (SEQ ID NO: 10)

The *Bacillus anthracis* and *B. cereus* Sasp-B
Sequence Alignment Showed a Significant
Difference, Namely a TAGCATT Insert BcerPub   1  AACAAAGCAACTTCTGGTGCTAGCAT-
TCAAAGTACAAATGCTAGTTATGGTACAGAGTTT
Banth 1 .....G..........................C.............
BcerPub 61 TCAACTGAAACAGATGTACAAGCTG-
TAAAACAAGCAAACGCACAATCAGAAG-
CAAAGAAA
Banth 61 G.G.........A..........A..............................T......
BcerPub 121 GCACAAGCTTCTGGTGCA------
CAAAGTGCAAACGCTAGTTATGGTACA-
GAATTTGCA
Banth 121 ..G..............TAGCATT.....CA....T.......................
BcerPub 175 ACTGAAACAGACGTGCATTCTGT-
GAAAAAACAAAATGCTAAGTCAGCTG-
CAAAACAA (SEQ ID NO: 11)
Banth 181 ...................G....................AC.A................ (SEQ ID NO: 12)

Conclusion from above results: Only the sasp-B sequence from *Bacillus anthracis* diverges from that of its near neighbor, *B. cereus,* to any useful extent. The sasp-2 sequences are identical, and the sasp-1 sequences differ too little to be of use in distinguishing the two organisms.

The underlined sequence TAGCATT (SEQ ID NO 107) represents an insertion region useful for distinguishing *Bacillus anthracis* from other *Bacillus species*.

EXAMPLE 4

Determination of Optimal Reaction Conditions for Maximal Sensitivity

By repeating the reaction condition optimization procedure described in Example 2 above, but upon a dilution series of *Bacillus anthracis* DNA down to 10 picograms per reaction, conditions were identified which resulted in maximum reaction sensitivity and specificity (as judged by the appearance of reaction products in ethidium bromide stained gel electrophoresis). By the criteria described, the best combination of conditions for use of BcSasp-B primers were as follows:

In a 100 microliter reaction volume the final concentration of reactants were 10 millimolar tris buffer pH 8.3; 25 millimolar potassium chloride; 2 millimolar magnesium chloride; 0.2 millimolar each dinucleotide triphosphate dATP, dCTP, dGTP, and dTTP; 50 picomoles of each primer, 5 units of Taq polymerase (Perkin Elmer, Norwalk, Conn.). Thermalcycling conditions were the same as those described in Example 2 above.

By viewing products with ethidium bromide stained gel electrophoresis it was determined that amplification specificity using these primers was quite good (only the expected product band and primers were visible), and product was visible down to 100 picograms per reaction.

EXAMPLE 5

Addressing the Necessary Question: How Conserved is the Sasp-B sequence in *Bacillus anthracis?*

In order to establish how conserved the promising stretch of *Bacillus anthracis* sasp-B gene sequence is, DNA from a variety of *B. anthracis* isolates was amplified and the amplicons sequenced. We acquired DNA from 38 geographically diverse anthrax isolates which was prepared by staff of the Centre for Applied Microbiological Research, Porton Down, UK from the collection of Dr. Peter Turnbull. DNA from the 38 isolates was amplified using the *B. cereus* sasp-B primers and the (optimized) reaction conditions described in Example 4. The resulting PCR product was sequenced and analyzed as described above. The results presented in FIG. 5 below confirmed that not only is the six base insertion present in diverse isolates of *Bacillus anthracis*, but the sequence as a whole is quite well conserved.

Referring now to FIGS. 1A–C, there is illustrated the results of the CLUSTAL W alignment of 38 different *B. anthracis* strains, with the sequence of interest underlined in line 38. It is conserved in all strains. The table below sets forth the identification of the various strains used:

TABLE 1

| Legend: Bacteria | ASC# | NMRI# | Designation | Description or ATCC# |
|---|---|---|---|---|
| *Bacillus anthracis* | | | Bapast | Institute Pasteur strain |
| *Bacillus anthracis* | | | Barec1 | UM23, Thorne strain |
| *Bacillus anthracis* | 152 | 1 | NMRI#1 | Namibia, 88 |
| *Bacillus anthracis* | BA40D | 2 | NMRI#2 | |
| *Bacillus anthracis* | 92 | 4 | NMRI#4 | Zambia, hippo, and passaged mouse, 88 |
| *Bacillus anthracis* | 30 | 5 | NMRI#5 | Shropshire, acquired, 79 |
| *Bacillus anthracis* | 273 | 6 | NMRI#6 | XingJiang Province China, 92 |
| *Bacillus anthracis* | 63 | 10 | NMRI#10 | Etosha, soil via guinea pig, 86 |
| *Bacillus anthracis* | BA42D | 11 | NMRI#11 | |
| *Bacillus anthracis* | 237 | 18 | NMRI#18 | Landkey, soil, mouse passage, 92 |
| *Bacillus anthracis* | 56 | 19 | NMRI#19 | Zimbabwe, human, 80 |
| *Bacillus anthracis* | 93 | 20 | NMRI#20 | Zambia, hippo, and passage guinea pig, 88 |
| *Bacillus anthracis* | | 22 | NMRI#22 | MS191 |
| *Bacillus anthracis* | 91 | 23 | NMRI#23 | Zambia, hippo, 88 |
| *Bacillus anthracis* | 11 | 24 | NMRI#24 | NCTC5444, London, 28 |
| *Bacillus anthracis* | 64 | 25 | NMRI#25 | Russian vaccine, Sterne |
| *Bacillus anthracis* | 29 | 26 | NMRI#26 | Waybridge, cow, traced to Senegal |
| *Bacillus anthracis* | 238 | 28 | NMRI#28 | Landkey, soil, 92 |
| *Bacillus anthracis* | 245 | 32 | NMRI#32 | Sterne |
| *Bacillus anthracis* | | 35 | NMRI#35 | 1 + 2 + DMD |
| *Bacillus anthracis* | 234 | 36 | NMRI#36 | Wessex, soil, 92 |
| *Bacillus anthracis* | | 38 | NMRI#38 | Rvacc |
| *Bacillus anthracis* | | 39 | NMRI#39 | PR13P |
| *Bacillus anthracis* | 264 | 40 | NMRI#40 | Zambia, contaminated soil, 91 |
| *Bacillus anthracis* | 43 | 41 | NMRI#41 | M36, passaged rabbits and rats |
| *Bacillus anthracis* | 69 | 42 | NMRI#42 | New Hampshire, 57 |
| *Bacillus anthracis* | 65 | 43 | NMRI#43 | Brazil, cow, acquired, 82 |
| *Bacillus anthracis* | 192 | 50 | NMRI#50 | Landkey, soil |
| *Bacillus anthracis* | 4 | 52 | NMRI#52 | M36, passaged in rabbits |
| *Bacillus anthracis* | 3 | 53 | NMRI#53 | M36, derived from original challenge stock |
| *Bacillus anthracis* | 2 | 54 | NMRI#54 | Griunard, 1950s |
| *Bacillus anthracis* | 54 | 55 | NMRI#55 | Zimbabwe, human, 80 |
| *Bacillus anthracis* | | 56 | NMRI#56 | 1 + 2 − |
| *Bacillus anthracis* | 28 | 59 | NMRI#59 | Waybridge, cow, traced to Senegal, 78 |

NMRI is the Naval Medical Research Institute, Bethesda, Maryland
ATCC is the American Type Culture Collection
ASC is The Association Of Systematics Collections

EXAMPLE 6

Scrutinizing the Sequence of BcSasp-B Primed Amplicons from *Bacillus anthracis* Near Neighbors Following reports that other labs had mistakenly identified *B. thuringiensis* as *Bacillus anthracis*, 24 serotypes of *B. thuringiensis* were obtained in order to check whether the sequence of sasp-B amplicons resembled those of other amplicons. DNA was prepared from *B. thuringiensis* as well as *B. cereus* liquid cultures following the method described by Zhou (Zhou, J., Bruns, M., and Jiedje, J. 1996. "DNA recovery from soils of diverse composition." Appl. Environ. Microbiol. 62:316–322), and amplified 100 nanograms of the DNA using *B.cereus* sasp-B primers. Product fragments were gel purified, extracted, sequenced, and analyzed as described in Example 3 above. The resulting alignment (FIG. 2) includes *B. thuringiensis* and *B. cereus* sasp-B sequences as well as *Bacillus anthracis* sasp-B sequence from the previous example:

Referring now to FIGS. 2A, 2B, and 2C, the 37 different sequences shown share a common difference, namely an insert in sequence NMRI#11 which is unique to that sequence. The identities of the sequences are shown in Table 2 below:

TABLE 2

Legend:

| Bacteria | BGSC# | Serotype | | Designation |
|---|---|---|---|---|
| *Bacillus licheniformis,* | | 5A2 | | 5A2 |
| *Bacillus thuringiensis* | | 4A1 | serot-1 | 4A1 |
| *Bacillus thuringiensis* | | 4A3 | cry (thur) serot-1 | 4A3 |
| *Bacillus thuringiensis* | | 4J2 | aizawai, pacificus/serot-7 | 4J2 |
| *Bacillus thuringiensis* | HD3 | 4B2 | 2 standard | BtB |
| *Bacillus thuringiensis* | HD4 | 4C3 | 3a standard | BtC |
| *Bacillus thuringiensis* | HD7 | 4E2 | 4a4b dendrolimus standard | BtE2 |
| *Bacillus thuringiensis* | | 4E4 | 4a4b | BtE4 |
| *Bacillus thuringiensis* | HD29 | 4G5 | 5a5b | BtG |
| *Bacillus thuringiensis* | HD10 | 4I1 | 6 | BtI |
| *Bacillus thuringiensis* | HD11 | 4J4 | 7 | BtJ |
| *Bacillus thuringiensis* | HD12 | 4K1 | 8 standard | BtK |
| *Bacillus thuringiensis* | HD537 | 4L3 | 9 standard | BtL |
| *Bacillus thuringiensis* | HD146 | 4M1 | 10 standard | BtM |
| *Bacillus thuringiensis* | HD201 | 4N1 | 11 antisera standard | BtM |
| *Bacillus thuringiensis* | HD542 | 4O1 | 12 standard | BtO |
| *Bacillus thuringiensis* | HD395 | 4P1 | 13 standard | BtP |
| *Bacillus thuringiensis* | ONR60A | 4Q1 | 14 | BtQ |
| *Bacillus thuringiensis* | HD511 | 4R1 | 15 | BtR |
| *Bacillus thuringiensis* | HD521 | 4S2 | 16 standard | BtS |
| *Bacillus thuringiensis* | HD525 | 4T1 | no flagellar antigen | BtT |
| *Bacillus thuringiensis* | HD541 | 4U1 | 11a11c | BtU |
| *Bacillus thuringiensis* | | 4V1 | 17 | BtV |
| *Bacillus thuringiensis* | HD 867 | 4W1 | 18 | BtW |
| *Bacillus thuringiensis* | IS720 | 4X1 | 21 | BtX |
| *Bacillus thuringiensis* | HD868 | 4Y1 | 19 standard | BtY |
| *Bacillus thuringiensis* | HD501 | 4Z1 | 8a8c standard | BtZ |
| *Bacillus anthracis* | BA42D | 11 | | NMRI#11 |
| Unidentified Bacillus | | | | 003 |
| Unidentified Bacillus | | | Taken from filled bag in "final mixing trailer" | 1B |
| Unidentified Bacillus | | | Isolated from 1B culture as morphologically distinct colonies | 1B/A |
| Unidentified Bacillus | | | Isolated from 25 kg media drum, bentonite mixture | III |
| Unidentified Bacillus | | | Isolated from bentonite spore stock | IV |
| *Bacillus cereus* | Genbank #M16813 | | NCBI Genbank database | Bcerpub |
| *Bacillus cereus* | ATCC 14579 | | Purchased from ATCC | Bcer1 |
| *Bacillus cereus* | ATCC 11778 | | Purchased from ATCC | Bcer2 |
| *Bacillus cereus* | ATCC 6464 | | Purchased ftom ATCC | Bcer3 |

BGSC is the Bacillus Genetic Stock Center, at The Ohio State University

Conclusion from the above sequence alignment: The single *Bacillus anthracis* sequence in the above alignment (#37 which is the bottom row of FIGS. 2A, 2B, & 2C) shows a unique pattern of sequence divergent from the sasp-B sequence of these near neighbor isolates.

Based on the DNA sequence information in FIGS. 1 and 2, amino acid sequences were extrapolated and evaluated for the sasp-B genes from *Bacillus anthracis, Bacillus cereus* and *Bacillus thuringiensis*. These extrapolated sequences are shown below in an extrapolated amino acid sequence alignments for the sasp-B gene from *Bacillus anthracis, Bacillus cereus* and *Bacillus thuringiensis*

TABLE 3

Legend:

| Bacteria | BGSC# | Serotype | Designation |
|---|---|---|---|
| *Bacillus thuringiensis* | type strain | | 4D4 |
| *Bacillus thuringiensis* | HD12 | 4K1 8 standard | BtK |
| *Bacillus thuringiensis* | HD3 | 4B2 2 standard | BtB |
| *Bacillus cereus* | published sequence | GenBank #M16813 | Bcerp |
| *Bacillus mycoides* | | ATCC 6421, | Bmyc |

```
          1              15 16             30 31             45 46           60
1 4D4     NKATSGASIQSTNAS YGTEFSTETDVQAVK QANAQSEAKKAQASG A-  QSANASYGTEFA
2 Bcep    NKATSGASIQSTNAS YGTEFSTETDVQAVK QANAQSEAKKAQASG A-- QSANASYGTEFA
3 BtK     NKATSGASIQSTNAS YGTEFATETNVQAVK QANAQSEAKKAQASG A-- QSANASYGTEFA
4 BtB     NKATSGASIQSTNAS YGTEFSTETDVQAVK QANAQSEAKKAQASG A-- QSANASYGTEFA
5 Banth   NKATSGASIQSTNAS YGTEFATETNVQAVK QANAQSEAKKAQASG ASIQSTNASYGTEFA
6 Bmyc    NKATSGASIQSTNAS YGTEFATETNVQAVK QANAQSEAQKAQASA A-- QSANASYGTEFA 61             75 76
1 4D4     TETDVHSVKKQNAKS AAKQ (SEQ ID NO:88)
2 Bcep    TETDVHSVKKQNAKS AAKQ (SEQ ID NO:89)
3 BtK     TETDVHAVKKQNAKS AAKQ (SEQ ID NO:90)
4 BtB     TETDVHAVKKQNAQS AAKQ (SEQ ID NO:91)
5 Banth   TETDVHAVKKQNAQS AAKQ (SEQ ID NO:92)
6 Bmyc    TETDVHAVKKQNAQS AAK  (SEQ ID NO:93)
```

TABLE 3-continued

Legend:

| Bacteria | BGSC# | Serotype | Designation |
|---|---|---|---|
| Bacillus anthracis | | subtype Flugge | Banth |

EXAMPLE 7

Design and Evaluation of Primers and Probes to Bacillus anthracis Specific Sasp-B DNA Sequence In the previous examples, the BcSasp-B primers were useful for evaluating the prevalence of the unique Bacillus anthracis sasp-B signature, but sequencing was required to distinguish amplicons of the several Bacillus species which could be amplified using the Bacillus cereus primers. By studying the alignment of Bacillus anthracis and Bacillus cereus sasp-B sequences (above) potential anthracis specific primer and probe sites were identified (shown below, SEQ ID NO: 94 and 95). Eight oligonucleotides were designed with the aid of Oligo 4.0 and BLAST database search utilities then synthesized (all as described in Example 1 above) and evaluated experimentally in various combinations for their ability to prime amplification of Bacillus anthracis only, using a panel of near neighbor Bacillus species. Three of the primer pairs were designed to incorporate the Bacillus anthracis insertion region into the three prime end of one primer per pair. This strategy greatly limited amplicon size and did not leave any Bacillus anthracis specific sequence for probe design.

The combination of primers originally designated BaSPB7 and BaSPB8 (below) were sufficiently specific. From 100 nanograms B. cereus target a very faint product band of nearly (but not exactly) the correct size, was evident; when compared to signals from an amplified dilution series of Bacillus anthracis DNA, the signal from Bacillus cereus was approximately equivalent to product from 10 picograms—indicating 10,000 fold less efficient amplification. Bands were not visible at or near the correct size from products of Bacillus coagulans, Bacillus circulans, Bacillus globigii, Bacillus mycoides, Bacillus subtilis or Bacillus thuringiensis amplification.

In addition, these primers were for sequences flanking, rather than incorporating the Bacillus anthracis insertion region, thus leaving this region within the product for binding to probes designed to hybridize to this unique signature.

The Bacillus anthracis Primer Data (from Analysis by Oligoprimer Design Software, National Biosciences, Plymouth, Minn.) is Summarized as Follows BaSPB7 primer sequence:
5' GTT ATG GTA CAG AGT TTG CG 3' (SEQ ID NO: 94)
Tm=57.4° C. (salt 1000.0 mM; oligo 0.6 pM)
Td=57.6° C., ΔG(25° C.)=−34.7 kcal/mol, Mr=6283
Ext. coeff.: 5.05 nmol/A260, 31.7 µg/A260
BaSPB8 primer sequence:
5' TTG TTT TGC AGC TGA TTG T 3' (SEQ ID NO: 95)
Tm=58.3° C. (salt 1000.0 mM; oligo 0.6 pM)
Td=58.9° C.,ΔG(25° C.)=−34.1 kcal/mol, Mr=5911
Ext. coeff.: 5.82 nmol/A260, 34.4 µg/A260

Optimal amplification conditions were determined in the same manner described in Examples 2 and 4 above. Optimal amplification conditions were identified as follows:

Thermalcycling: Amplifications were performed in a Perkin Elmer 9600 thermocycler with the following thermal cycling regime: 94° C. for 5 minutes, then 40 repeating cycles of 94° C. for 30 seconds, 50° C. for 30 seconds and 72° C. for 30 seconds, followed by a 7 minute 72° C. final extension step.

Reaction mixture: Each 100 ul reaction contained 0.1 millimolar each dATP, dCTP, dGTP and dTTP, 25 picomoles each primer, 10 millimolar Tris-HCl pH 8.3, 2 millimolar $MgCl_2$, 25 millimolar KCl, 2.5 units of Taq polymerase (Perkin Elmers, Norwalk, Conn.) and 100 ng or less of template DNA.

The Uniqueness of these Primers may be Seen by a Bacillus anthracis and Bacillus cereus Sasp-B Sequence Alignment Emphasizing Bacillus anthracis Specific Primer Sequences:

```
BcerPub   1 AACAAAGCAACTTCTGGTGCTAGCATTCAAAGTACAAATGCTAGTTATGGTACAGAGTTT
Banth     1 .....G....................C..........GTTATGGTACAGAGTTT
                                                    --primer BaSPB7--

BcerPub  61 TCAACTGAAACAGATGTACAAGCTGTAAAACAAGCAAACGCACAATCAGAAGCAAAGAAA
Banth    61 GCG.........A..........A.............................T......
            -->

BcerPub 121 GCACAAGCTTCTGGTGCA------CAAAGTGCAAACGCTAGTTATGGTACAGAATTTGCA
Banth   121 ..G.............TAGCATT.....CA....T........................

BcerPub 175 ACTGAAACAGACGTGCATTCTGTGAAAAAACAAATGCTAAGTCAGCTGCAAAACAAA       (SEQ ID NO: 96)
Banth   181 ..................G...................ACAATCAGCTGCAAAACAAA    (SEQ ID NO: 97)
                                                   <--primer BaSPB8-
```

EXAMPLE 8

Selection and Evaluation of Probes for Detection of Bacillus anthracis Sasp-B Amplicons Three of the oligonucleotides evaluated as primers incorporated the Bacillus anthracis specific insertion region, and having designed primers flanking the insertion region, these oligos were tested as probes to confirm the identity of the amplicons; only amplicons from B. anthracis would include the 6 base insertion, as follows:

Alignment of Bacillus cereus and Bacillus anthracis Sasp-B Sequences Emphasizing Probed Locations

```
Bcer   AACAAAGCAACTTCTGGTGCTAGCATTCAAAGTACAAATGC
Banth  AACAAGGCAACTTCTGGTGCTAGCATTCAAAGCACAAATGC Bcer   TAGTTATGGTACAGAGTTTTCAACTGAAACAGATGTACAAGCTGTAAAACAAGCAAACGCACAA
Banth  TAGTTATGGTACAGAGTTTGCGACTGAAACAAATGTACAAGCAGTAAAAAAGCAAACGCACAAT Bcer   TCAGAAGCAAAGAAAGCACAAGCTTCTGGTGCA------AAAGTGCAAACGCTAGTTATGGTACAGAATTTGCAA
Banth  CAGAAGCTAAGAAAGCGCAAGCTTCTGGTGCTAGCATTCAAAGCACAAATGCTTTGCATAGTTATGGTACAGAAA
                          --------------------
                          --------------------
                          ↑ location of probes tested ↑

Bcer   CTGAAACAGACGTGCATTCTGTGAAAAAACAAAATGCTAAGTCAGCTGCAAAACAA (SEQ ID NO:98)
Banth  CTGAAACAGACGTGCATGCTGTGAAAAAACAAAATGCACAATCAGCTGCAAAACAA (SEQ ID NO:99)
```

Three Oligonucleotides Evaluated for use as *Bacillus anthracis* Probes:

BaSPB2: (inverted, 'lower strand' sequence): 5' GCATTTGTGCTTTGAATGCTA 3' (SEQ ID NO: 100)
BaSPB4: (inverted, 'lower strand' sequence): 5° CATTTGT-GCTTGTAATGCTA 3' (SEQ ID NO: 101)
BaSPB5: (direct, 'upper strand' sequence): 5' AGCTTCTG-GTGCTAGCATT 3' (SEQ ID NO: 102)

Oligos (shown above) were tested as probes in the following manner:

*Bacillus anthracis* DNA (100 nanograms per 100 microliter reaction of the Sterne strain) was amplified using Biotin labeled BaSPB7 and BaSPB8 primers which had been synthesized to our order by Life Technologies (Gaithersburg, Md.).

Following the instructions for the Universal GeneComb Kit (Bio-Rad, Richmond, Calif.), 8 picomoles and 5 picomole quantities of each oligo (henceforth called probe) in the kit binding buffer was spotted on the GeneComb test kit card nitrocellulose surface, and bound to the nitrocellulose using the UV Stratalinker 1800 (Stratagene, La Jolla, Calif.) set to auto crosslink mode. The biotinylated amplicon was denatured, and allowed to migrate across the (bound) probe spots, hybridizing to them in the process. The resulting bound biotinylated hybrid was then reacted with the kit streptavidin/alkaline phosphatase conjugate followed by kit chromogenic substrate-enabling visualization of the probe/amplicon hybrids. Evaluation of the test spot signal intensity guided the choice of probe for further evaluation. BaSPB4 proved most sensitive in this test, so succeeding work was done with this probe.

In order to roughly gauge sensitivity of the system: Amplification was performed using Biotinylated BaSPB7 and BaSPB8 primers, the target(s) being a dilution series of *Bacillus anthracis* DNA (Sterne strain) whose concentration (prior to dilution) had been carefully determined using the Beckman DU 640 Spectrophotometer. The dilutions amplified were (total input per 100 microliter reaction): 10, 5, and 1 picogram(s), 100, 50, and 20 femtograms. Following the GeneComb test kit instructions, one tenth of each PCR was reacted with (bound) BaSPB4 and the resulting hybrids 'developed'. The developed test strips reflected the input DNA dilutions in color intensity, with even the 20 femtogram reaction yielding a visible spot. (Data not shown.) The results comprised a visible spot for each dilution tested (10 pg down to 20 fg), with the negative PCR and kit control showing no spots.

Finally, probe BaSPB4 was tested for specificity. Fifty nanograms of DNA from each of the following *Bacillus species* was amplified using biotinylated BaSPB7 and BaSPB8: *Bacillus anthracis, Bacillus thuringiensis, Bacillus cereus, Bacillus mycoides, B. subtilis, Bacillus globigii*. The denatured amplicon of each DNA species was reacted against the bound BaSPB4 probe and the test strips developed. Only the *Bacillus anthracis* amplicon resulted in any signal (which was quite intense); none of the other species bound to the probe in order to result in a signal. Conclusion: BaSPB4 binds *Bacillus anthracis* DNA specifically. BaSPB4 binding specificity was demonstrated with the BioRad universal GeneComb System (data not shown). 100 ng of each species of DNA amplified was placed on each panel, as follows (1–8):

Species Amplified:
1) *Bacillus anthracis*
2) *Bacillus thuringiensis*
3) *Bacillus cereus*
4) *Bacillus mycoides*
5) *Bacillus subtilis*
6) *Bacillus globigii*
7) Negative PCR
8) Kit positive control The *Bacillus anthracis* showed a large spot; the other panels were blank, except for the positive control. This showed that only the amplified *Bacillus anthracis* sasp B sequence reacted with the probe.

Some Potential Detection Systems for the *Bacillus anthracis* Specific Primer/Probe System The primer/probe system described above is ideally suited to the 5'nuclease fluorescence homogeneous assay in which the accumulation of specific amplicon is monitored as fluorescence is released from the probe by Taq polymerase during the amplification of target DNA to which the probe anneals. This system is described in U.S. Pat. Nos. 5,538,848; 5,723,591; and 5,876,930, hereby incorporated by reference.

The primer/probe system described is also suited to amplification followed by separate hybridization of biotinylated amplicon molecules to bound probe in a colormetric microwell plate type assay (J. Mulder, N. McKinney, C. Christopherson, J.Sninsky, L. Greenfield and S. Kwok. Rapid and Simple PCR Assay for Quantitation of HIV-I RNA in Plasma: Applications to Acute Retroviral Infection. J. Clin. Micro. 37(2): 292–300, 1994); or, in similar manner, as with the automated AmpliCore integrated PCR+detection devices (Roche, Pleasanton, Calif.), and as described, a simple dot blot type assay.

There is an increasing number of PCR devices and coordinated detection strategies; the primers/probes and amplification system described are robust, specific, and sensitive enough to be adapted to most of these.

Regardless of detection format, the described assay could be used to monitor the presence of anthrax in the environment (such as for investigation by military and law enforcement agencies of clandestine production of anthrax for illicit use; for Public Health and law enforcement agencies to test suspicious spore-like powders; to check for anthrax in suspected cases of bio-terrorist attack).

This assay is also well suited as a rapid, specific, and sensitive method for detecting anthrax in biological fluids such as blood, sputum, and feces in clinical and Public Health labs, as well in the field, and for autopsies.

EXAMPLE 9

Development of *Bacillus globigii* Specific PCR Based on Sasp Gene Sequence

In the same manner as described in Example 1 above, a sasp gene (sasp-gamma in this case) sequence was identified for the production of primers specific for *Bacillus globigii* sequence. Primers and amplification conditions were designed (see FIG. 3) for heterologous PCR based on published sequence for the *Bacillus subtilis* sasp E gene (sasp-gamma) acquired from GenBank (accession number M16184). After sequencing amplicons from *Bacillus globigii* (generated using the *Bacillus subtilis* primers), and aligning *Bacillus globigii* sequence with the published *Bacillus subtilis* sequence, *Bacillus globigii* specific primers were designed taking advantage of the differences in the sequence. After searching the databases to be sure that the new *Bacillus globigii* primers were not homologous to other sequences, and optimizing amplification conditions, a panel of Bacillus species were amplified to check primer specificity. Amplicons of the correct size were produced only from Bacillus designated as *Bacillus globigii*, for all but the most arcane intents and purposes (there is disagreement among a very few researcher as to whether *Bacillus subtilis* niger and *Bacillus atrophaeus* are, in fact, genetically different from *Bacillus globigii* at all); importantly, the new primers did not amplify *Bacillus subtilis* or *Bacillus amyloliquifaciens* which are distinct species, yet very closely related to *Bacillus globigii*. Referring now to FIG. 3, there is shown an alignment of *Bacillus subtilis* sasp-gamma sequence (from Genbank) (Bs_pub_SSPE) with *Bacillus globigii* sequence (upper strand) showing the location of the primer sequences and how their sequence compares to the known *Bacillus subtilis* sequence.

The BgSaspGam primers produce *B globigii* specific PCR product, as was demonstrated in an Nuseive-Agarose gel (data not shown). The gel showed approximately a 135b *Bacillus globigii* specific amplicon. No amplification of negative controls in *Bacillus cereus; Bacillus amyoliquifaciens, Bacillus megaterium,* or *Bacillus globisporus* was observed. Amplification was observed with *Bacillus atropheus* (ATCC 6455 and 49337) and *Bacillus niger.* It should be noted that *Bacillus subtilis* niger and *Bacillus atrophaeus* have been officially designated *Bacillus globigii* since they are virtually indistinguishable from *Bacillus globigii* at the molecular level. Near neighbors *Bacillus subtilis, Bacillus globisporous* and *Bacillus megatarium* do not amplify with the BgSaspGam primers.

*Bacillus globigii* Sasp-gamma Primers

BgSaspGam 5' 5' ACATGGCTAACTCAAACAACAA 3' (SEQ ID NO: 103)
BgSaspGam 3' 5' GGTTTTGTTTTCTTACTTGTTGTAC 3' (SEQ ID NO: 104)

Reaction conditions successfully employed using the above primers:

Reaction mixture composition: In a 100 microliter reaction volume the final concentration of reactants were 10 millimolar tris buffer pH 8.3; 25 millimolar potassium chloride; 2 millimolar magnesium chloride; 0.2 millimolar each dinucleotide triphosphate dATP, dCTP, dGTP, and dTTP; 50 picomoles of each primer, 5 units of Taq polymerase (Perkin Elmer, Norwalk, Conn.).

Thermalcycling conditions using TC9600 (Perkin Elmer, Norwalk, Conn.): A 5 minute 94 degree C. initial denaturation step was followed by 40 three step cycles of 94 degrees C. for 30 sec., 50 degrees C. for 30 sec., 72 degrees C. for 30 sec. A final extension step of 7 minutes at 72 degrees C. completed the thermalcycling.

There a number of potential uses of the research *Bacillus globigii* specific amplification system. *Bacillus globigii* is used as a nonpathogenic surrogate, replacing *Bacillus anthracis*, for purposes of modeling aerosol spore distribution under various environmental conditions, as well as for testing spore collection hardware. The agencies carrying out these endeavors have had trouble finding a way of detecting only the *Bacillus globigii* used in their experiments; detection systems have been non-specific, resulting in false alarms and compromised data.

EXAMPLE 10

Development of Clostridium Perfringens PCR Based on Sasp Gene Sequence

In a manner similar to the above descriptions, a sasp gene (sasp-2 in this case) sequence was identified for the production of primers for amplification of *Clostridium perfringens* sequence. Primers and amplification conditions were designed and carried out using *Clostridium perfringens* DNA. While amplification successfully produced product of the correct size (when viewed by ethidium bromide gel electrophoresis), near neighbor DNA has yet to be evaluated in order to assess specificity of these primers.

*Clostridium perfringens* Sasp-2 Primers

CPssp2-1: 5' AATAACTAAGGAGGAATGAAAAATGT 3' (SEQ ID NO: 105)
Cpssp2-2: 5' TTGTTCTACCATTCTTTTAACCATT 3' (SEQ ID NO: 106)

The following reaction conditions were successfully employed using the above primers:

Reaction mixture composition: In a 100 microliter reaction volume the final concentration of reactants were 10 millimolar tris buffer pH 8.3; 25 millimolar potassium chloride; 2 millimolar magnesium chloride; 0.2 millimolar EACH dinucleotide triphosphate dATP, dCTP, dGTP, and dTTP; 50 picomoles of each primer, 5 units of Taq polymerase (Perkin Elmer, Norwalk, Conn.).

Thermalcycling conditions using TC9600 (Perkin Elmer, Norwalk, Conn.): A 5 minute 94 degree C. initial denaturation step was followed by 40 three step cycles of 94 degrees C. for 30 sec., 50 degrees C. for 30 sec., 72 degrees C. for 30 sec. A final extension step of 7 minutes at 72 degrees C. completed the thermalcycling.

There are a number of potential uses of *Clostridium perfringens* specific PCR. *Clostridium perfringens* is officially listed as a biological weapon agent, so uses would be similar to those described for the *Bacillus anthracis* specific primers.

Also, using these primers for heterologous PCR of *Clostridium botulinum* (a serious health threat and potential biological weapon) in order to acquire sequence information for the design of primers specific to that organism. Such primers, and any probe so identified in the process, would also be useful in the same manner described for the *Bacillus anthracis* specific detection research system described above.

Having described the present invention according to the presently preferred embodiment, it will be apparent that other embodiments are possible in light of the present teachings. For example, other DNA amplification methods besides PCR are known, such as the Q-beta replicase method. Certain of these methods may be used in a single-step amplification/detection protocol, based, for example, on the unique *Bacillus anthracis* sasp-B insertion AGCATT (SEQ ID NO 112).

Accordingly, the present invention should be understood to encompass subject matter limited only by the scope of the appended claims.

What is claimed is:

1. A PCR primer useful in detecting *Bacillus anthracis*, comprising the sequence:
5' GTT ATG GTA CAG AGT TTG CG 3' (SEQ ID NO. 94).

2. A PCR primer useful in detecting *Bacillus anthracis*, comprising the sequence:
5' TTG TTT TGC AGC TGA TTG T 3' (SEQ ID NO. 95).

3. A method for specifically detecting a DNA sequence from *Bacillus anthracis* comprising the steps of:
   (a) providing a DNA sample;
   (b) incubating the DNA sample with primers comprising the sequences:
      5' GTT ATG GTA CAG AGT TTG CG 3' (SEQ D NO. 94) and
      5' TTG TTT TGC AGC TGA TTG T 3' (SEQ D NO. 95);
   (c) amplifying DNA hybridizing to said primers; and
   (d) detecting the presence of any amplified product, whereby only DNA from *Bacillus anthracis* is amplified and detected.

4. The method of claim 3 wherein said detecting is done with a probe comprising a sequence selected from the group consisting of:
5' TAGCATT 3' (SEQ ID NO: 107) and 5' AATGCTA 3' (SEQ ID NO.108).

5. The method of claim 4 wherein said probes are selected from the group consisting of
5' TAGCATTCAAAGCACAAATG 3' (SEQ ID NO. 109) and
5' CATTTGTGCTTTGAATGCTA 3' (SEQ ID NO. 101).

6. A PCR primer useful in detecting *Bacillus globigii*, consisting of the sequence:
5' ACA TGG CTA ACT CAA ACA ACA A 3' (SEQ ID NO. 103).

7. A PCR primer useful in detecting *Bacillus globigii*, comprising the sequence:
5' GGT TTT GTT TTC TTA CTT GTT GTA C 3' (SEQ ID NO 104).

8. A method for specifically detecting a DNA sequence from *Bacillus globigii*, comprising the steps of:
   (a) providing a DNA sample;
   (b) incubating the DNA sample with primers comprising the sequences:
      5' ACA TGG CTA ACT CAA ACA ACA A 3' (SEQ ID NO. 103) and
      5' GGT TTT GTT TTC TTA CTT GTT GTA C 3' (SEQ ID NO. 104);
   (c) amplifying DNA hybridizing to said primers; and
   (d) detecting the presence of any amplified product, whereby only DNA from *Bacillus globigii* is amplified and detected.

9. A PCR primer useful in detecting *Clostridium perfringens*, consisting essentially of the sequence:
5' AAT AAC TAA GGA GGA ATG AAA AAT GT 3' (SEQ ID NO. 105).

10. A PCR primer useful in detecting *Clostridium perfringens*, consisting essentially of the sequence:
5' TTG TTC TAC CAT TCT TTT AAC CAT T 3' (SEQ ID NO. 106).

11. A method for specifically detecting a DNA sequence from *Clostridium perfringens*, comprising the steps of:
   (a) providing a DNA sample;
   (b) incubating the DNA sample with primers consisting essentially of the sequences:
      5' AAT AAC TAA GGA GGA ATG AAA AAT GT 3' (SEQ ID NO.105) and
      5' TTG TTC TAC CAT TCT TTT AAC CATT 3' (SEQ ID NO. 106);
   (c) amplifying DNA hybridizing to said primers; and
   (d) detecting the presence of any amplified product, whereby DNA from *Clostridium perfringens* is amplified and detected.

12. A cloned and isolated nucleic acid encoding a *Bacillus globigii* sasp-gamma polypeptide comprising the sequence recited in SEQ ID NO 110.

13. A primer which amplifies specifically SEQ ID NO: 110 recited in claim 12.

14. A method for the detection of *Bacillus globigii* in a sample, comprising the steps of:
   (a) specifically incubating the sample with amplification primers that hybridize to the *Bacillus globigii* sasp-gamma gene;
   (b) amplifying hybridized primers; and
   (c) detecting the presence of amplified *Bacillus globigii* sasp-gamma gene sequences.

15. A primer which hybridizes completely to the sequence SEQ ID NO: 110 and which is capable of amplifying specifically SEQ ID NO: 110.

* * * * *